(12) United States Patent
Smith

(10) Patent No.: US 7,599,062 B2
(45) Date of Patent: Oct. 6, 2009

(54) LOCAL NON-PERTURBATIVE REMOTE SENSING DEVICES AND METHOD FOR CONDUCTING DIAGNOSTIC MEASUREMENTS OF MAGNETIC AND ELECTRIC FIELDS OF OPTICALLY ACTIVE MEDIUMS

(76) Inventor: Roger Smith, 12739 Vista Dr., Bainbridge Island, WA (US) 98110

( * ) Notice: Subject to any disclaimer, the term of this patent is extended or adjusted under 35 U.S.C. 154(b) by 194 days.

(21) Appl. No.: 11/900,948

(22) Filed: Sep. 14, 2007

(65) Prior Publication Data

US 2009/0073442 A1    Mar. 19, 2009

(51) Int. Cl.
*G01J 4/00*    (2006.01)
(52) U.S. Cl. .................................................. 356/367
(58) Field of Classification Search ................... 356/367
See application file for complete search history.

(56) References Cited

U.S. PATENT DOCUMENTS 4,560,279 A * 12/1985 Kouns ........................ 356/369

* cited by examiner

*Primary Examiner*—Roy Punnoose
(74) *Attorney, Agent, or Firm*—Olympic Patent Works PLLC

(57) ABSTRACT

Embodiments of the present invention are directed to pulsed polarimeters for conducting remote, non-perturbative diagnostic measurements of inducing fields of a medium demonstrating induced optical activity. In one aspect, a pulse polarimeter includes a light source emitting a polarized light pulse having sufficiently narrow spatial extent at a prescribed wavelength and a light gathering optical system including a light gathering optic having an optic axis directed toward the medium and positioned to collect and collimate a predetermined solid angle of an emission from the medium into a collimated emission beam, while preserving the polarization state of the emission. The pulse polarimeter includes a directional coupler that makes coincident the propagation direction of the polarized light pulse with the optic axis and a polarization detection system for measuring the intensity and determining the polarization state of the collimated emission beam continuously in time as the polarized light pulse transits the medium.

20 Claims, 5 Drawing Sheets

LOCAL NON-PERTURBATIVE REMOTE SENSING DEVICES AND METHOD FOR CONDUCTING DIAGNOSTIC MEASUREMENTS OF MAGNETIC AND ELECTRIC FIELDS OF OPTICALLY ACTIVE MEDIUMS

TECHNICAL FIELD

Embodiments of the present invention are directed to devices and methods for remote non-perturbative and localized measurements of a field in an active medium.

BACKGROUND

A non-perturbative, spatially resolved measurement of the magnetic field deep within a high temperature magnetically confined plasma is very difficult and has only been achieved under special conditions at great effort. Just once, with a carefully tailored tokamak discharge and a special sensing apparatus has the internal magnetic field been directly detected, non-perturbatively, at a single location. See "Measurement of magnetic fields in a tokamak using laser light scattering" Forrest, M. G., Carolan, P. G. and Peacock, N. J. (1978). Nature 271:718. This one-off measurement has never been repeated. The prior art simply does not provide a devices or method that can be applied routinely or under general conditions to determine the local magnetic field.

In the field of plasma physics, relevant to magnetic fusion, knowledge of the magnetic field distribution throughout the plasma volume is crucial to understanding the key issues of magnetohydrodynamic ("MHD") stability and energy transport. Since the 1950's, a major international collaboration has developed employing many hundreds of scientists world wide to understand the dynamics of magnetic confinement of plasmas with the goal of achieving controlled thermonuclear fusion. The subject is of immense importance since the field has a direct impact on the future energy resources available to society. In this time, an experimental means of directly measuring the internal magnetic field structure has been highly sought after but has not yet been attained. Only for the well developed tokamak confinement device have multiple diagnostic systems produced detailed knowledge of the internal magnetic field structure but no direct measurements of such. The problem is that fusion relevant plasmas have temperatures of approximately 100 million° C. or greater, representing an extremely hostile environment for direct measurement techniques. The next generation of laboratory plasmas promises to be even more challenging with the addition of radiation hazards from the production of significant amounts of fusion energy and high neutron fluxes making remote sensing of plasma parameters essential. Many conventional plasma diagnostic systems cannot be adapted to the harsh radiation environment of such a plasma.

An experimental determination of the spatial variation of the magnetic field is important for a number of reasons. The knowledge of the internal magnetic field distribution is equivalent to knowing the current distribution in the plasma. Much importance is placed on measuring the mid-plane magnetic q-profile or magnetic shear from the edge to the center of the plasma. Advanced tokamak scenarios involve controlling the q-profile to stabilize destructive modes that grow and terminate the plasma discharge. At present, sophisticated equilibrium codes are used which rely on a large number of diagnostic measurements, mostly external magnetic measurements, to infer the q-profile but with poor accuracy, poor localization, and poor response time. A means of rapidly determining the q-profile, in real time, is needed for feedback purposes in order to detect the presence and location of a destructive MHD instability so that the current profile can be quickly adjusted. The magnetic shear for tokamak plasmas is typically everywhere positive; however, reversed magnetic shear discharges have lately been reported but direct evidence is lacking and magnetic profile measurements are needed. Recently, tokamak discharges with current-less cores have been reported, but again, direct evidence and profile measurements are needed. The need for a non-perturbative, spatially resolved measurement of the internal magnetic field is just as urgent and contemporary today as it was 50 years ago.

In order to gain an appreciation of the exceptional attributes of the present invention one must look at the resources and effort employed in the magnetic fusion field to determine the plasma state. The largest tokamak, the Joint European Tokamak ("JET") project, has an annual operating budget over $100 million. The main diagnostic systems in this discipline are: arrays of external magnetic field sensors (magnetic field probes, current and flux sensors), continuous wave ("CW") laser polarimetry and interferometry, Thomson scattering, coherent scattering, reflectometry, motional Stark effect ("MSE"), beam emission spectroscopy ("BES"), laser induced fluorescence ("LIF"), Langmuir probes, internal magnetic field probes, soft X-ray tomography, bremsstrahlung emission, electron cyclotron emission ("ECE") and magnetic field equilibrium codes ("EFIT"). For the plasma parameters the systems address, several are perturbative, several provide chord averaged measurements, and several are indirect being measurements outside the plasma volume but none provide a direct, non-perturbative measurement of a local magnetic field B. For larger tokamak experiments, most of the above systems are routinely used and correlated to infer local plasma parameters and indirectly, the local magnetic field inside the plasma. The next generation of larger devices are designed to have higher magnetic fields and higher plasma densities which, in general, pose more problems, especially for external measurements or diagnostics using beams: LIF, MSE, and BES and for material probes: magnetic field and Langmuir probes. The purely optical diagnostics are highly favored for future devices.

A short and necessarily incomplete overview of magnetic field sensing in plasmas follows. Material probes such as magnetic pickup coils have been successfully inserted into low temperature plasmas and measure the local magnetic field quite well. On fusion relevant devices, such probes poison the plasma, perturbing the plasma even when confined to the low temperature edge. Next, the CW polarimeter diagnostic exploits the magneto-optic activity known as the Faraday effect to measure a chord averaged electron density-(parallel) magnetic field product along the probe beam. The Faraday effect is only sensitive to the component of B parallel to the path of the probe beam, $B_\parallel$. The measurement is non-perturbative but non-local and the two parameters, electron density and magnetic field, cannot be separately determined. A CW polarimeter is usually combined with a laser interferometer to independently measure the chord averaged electron density along the same sightline. However the two chord averaged measurements cannot be combined to produce even a chord averaged magnetic field. Many CW polarimeter/interferometer sightlines are needed to resolve local details by tomographic means, a complex and costly proposition with a poor return on spatial resolution. Nevertheless, the CW polarimeter/interferometer diagnostic is considered essential on any large device. Today, the MSE diagnostic is being intensively pursued on mainstream tokamak devices as a viable direct measurement technique that can routinely provide local internal magnetic field measurements (q profiles). The MSE diagnostic requires a particle beam and so is perturbative. However, it has difficulty reaching deep locations in high temperature plasmas, suffers from low light levels, poor spatial and temporal resolution and its sightline is fixed to the particle beam. The MSE diagnostic is also difficult and expensive to implement and only viable on plasmas that are well understood and well diagnosed, essentially the tokamak. Lastly, magnetic equilibrium reconstruction can be used to infer the internal magnetic field distributions from magnetic field measurements (pickup coils, flux and current sensors) external to the plasma. The magnetic field is extrapolated from the outside inward. This technique is ill-conditioned only providing details just inside the plasma edge. Additional internal measurements of any plasma parameter significantly constrain the solution and inputs from all of the aforementioned diagnostics are used to more accurately determine local B. For plasmas that are not the mainstream tokamak or stellarator configurations, many of the above diagnostics are of much less utility. This is because the plasmas can be highly dynamic and transient, the plasma theory is less developed, the experimental access is different, the diagnostics are not amenable to the magnetic configuration or insufficient manpower is available. Nevertheless, these plasmas are important and are also being pursued as a means to achieve fusion energy.

The prior art that represents the present state of non-perturbative remote magnetic field sensing in plasmas is the well-known CW plasma polarimeter/interferometer instrument. That is not to say that CW plasma polarimetry/interferometry directly measures the magnetic field, far from it, but it does measure a quantity directly related to the magnetic field. The instrument measures the chord averaged electron density-(parallel)magnetic field product and the chord averaged density along a laser beam path (trajectory) through the plasma. From these two non-local measurements and assumptions about the density distribution, it is possible to draw some conclusions about the magnetic field distribution. In principle, if many such systems were employed, a local magnetic field and local density could be ascertained by tomographic means. For the required spatial resolution, such an undertaking would be out of the question, though multichord systems are in use.

FIG. 1 shows an isometric view of a schematic representation of a CW polarimeter/interferometer. The polarimetry part of the instrument includes, in elemental form, a light source 20, emitting a continuous polarized collimated beam 18, a directional coupler 26, and a polarization detection system 10. The CW polarimeter is sensitive to a magnetic field distribution 29 distributed in a remote magnetized plasma 28. The directional coupler 26 can be a non-polarizing beamsplitter. The light source 20 need not be coherent for polarimetry and is linearly polarized. Some fraction (50%) of the polarized collimated beam 18 is transmitted through the directional coupler 26, through the remote magnetized plasma 28, along a beam axis 24, retro-reflected by end mirror 22b, doubles back along the beam axis 24 and some fraction (50%) is reflected (redirected) by the directional coupler 26 toward the polarization detection system 10. A collimated output beam 25 is analyzed using a polarizing beam splitter 16 that spatially separates the collimated output beam 25 into two mutually orthogonal collimated analyzed output beams 15a,b. Focusing lenses 14a,b focus the collimated analyzed output beams 15a,b onto optical detectors 12a,b producing electrical signals (voltage or current) proportional to the intensity of the collimated analyzed output beams 15a,b. The rotation angle, $\alpha_{CW}$, of the polarization of the collimated output beam 25 relative to the polarization state of the light source 20 is measured. The result for a magnetized plasma with electron density distribution, $n_e$, and magnetic field distribution, B, is given by:

$$\alpha_{CW}(T) = 2 \times 2.63 \times 10^{-13} \lambda_o^2 \int_0^{L_p} (n_e B_{\parallel})(s, t(s)) ds \qquad \text{Eq. 1}$$

where $L_p$ is the length ("chord length") of the scene ("probe") beam 23 in the remote magnetized plasma 28 and $\lambda_o$ is the wavelength of the light source 20. For a probe beam propagating at the speed of light c($3 \times 10^8$ m/s), the explicit time dependence varies with location s, as t(s)=s/c. Eq. 1 can be interpreted as follows: the polarization of the probe beam rotates an angle $\alpha_{CW}(T)$ in the plane of polarization for a beam path (trajectory) in the magnetized plasma parameterized by path length, s, from the plasma edge (s=0) to the opposite edge, (s=$L_p$),—and back again, and varies proportionally to the line integrated $n_e B_{\parallel}$ product along the beam path. The time, T, is identified with the entire path integral, a duration of $2L_p$/c seconds. $B_{\parallel}$ and $n_e$ are generally time dependent but assumed constant (quasi-static) on a time scale of $2L_p$/c and t(s) can be replaced by T in Eq. 1. The chord averaged rotation angle is $<\alpha_{CW}>_{L_p}(T) = \alpha_{CW}(T)/2L_p$. Eq. 1 expresses the magneto-optic Faraday effect for magnetized plasmas using CW plasma polarimetry. The Faraday effect is exceptional in that the retro-reflected beam continues to accumulate rotation angle, doubling that of a single pass system. Eq. 1 is a simplified expression that assumes the frequency of the light source, $\nu_o(c/\lambda_o)$, is much higher than any cutoff frequency along the probe beam path. Without including interference from a reference beam 21, the optical detectors 12a,b are sensitive to the intensity in the collimated analyzed output beam 15a,b, conventionally labeled the s and p polarization channels. If the axis of the polarizing beam splitter 16 is oriented to be approximately 45° to the polarization of the light source, then the voltage difference, $(V_s - V_p)$, for balanced optical detectors 12a and 12b varies proportionally with $2\alpha_{CW}(T)I_o(T)$ for small $\alpha_{CW}(T)$ and the sum, $(V_s + V_p)$, to the total intensity, $I_o(T)$, of the collimated output beam 25. The proportionality constants are obtained from the measured responsivity (calibration) of the optical detectors 12a,b.

Typically, a CW plasma polarimeter is combined with a CW interferometer 19 to simultaneously measure the chord averaged electron density over the same probe beam path. The interferometry part of the instrument includes, in elemental form, the light source 20, emitting the continuous coherent polarized collimated beam 18, the interferometer 19 and the phase-sensitive polarization detection system 10. The light source need not be polarized for interferometry alone. The polarimeter/interferometer shown in FIG. 1 uses a laser as the coherent light source 20 emitting the continuous coherent polarized collimated beam 18 at a prescribed wavelength and incorporates an interferometer 19 including a reference beam 21 with end mirror 22a, a scene beam 23 with end mirror 22b and the directional coupler 26 (non-polarizing beam splitter). The scene beam 23 with the beam axis 24 intersects the remote magnetized plasma 28. The directional coupler 26 redirects the beam axis 24 and combines the scene and reference beams onto the phase sensitive polarization detection system 10 comprising the polarizing beam splitter 16 which analyzes and spatially separates the polarized collimated beam 18 into two mutually orthogonal collimated analyzed output beams 15a,b, focusing lenses 14a,b focuses the collimated analyzed output beams 15a,b onto optical detectors 12a,b producing electrical signals (voltage or current) proportional to the product of the electric field amplitudes of the reference and scene beams in their respective polarization channels. A relative phase difference between the reference and scene beams, due to the index of refraction of the remote magnetized plasma, produces an interference at the optical detectors. The optical detectors act as optical mixers and both the phase and amplitude of the interference is measured. The phase difference of either optical detector is given by:

$$\phi_{CW}(T) = 2 \times 4.5 \times 10^{-16} \lambda_o \int_0^{L_p} n_e(s, t(s)) ds \qquad \text{Eq. 2}$$

Eq. 2 can be interpreted as follows: the phase difference between the reference beam and the scene beam, $\phi_{CW}(T)$, for a path in the remote magnetized plasma parameterized by path length, s, from the plasma edge (s=0) to the opposite edge, (s=$L_p$), varies proportionally to the line integrated $n_e$ along the path. The chord averaged phase is $<\phi_{CW}>_{Lp}(T) = \phi_{CW}(T)/2L_p$ which yields a chord averaged electron density. The time, T, is identified with the entire path integral, a duration of $2L_p/c$ seconds where $n_e$ is assumed quasi-constant on a time scale of $2L_p/c$ seconds.

For the combined CW polarimeter/interferometer instrument, the amplitudes of the interference for both s and p channels are used to determine the polarization state of the collimated output beam 25, $\alpha_{CW}(T)$. The difference in the amplitudes of the optical detector voltages for balanced detectors, $<V_s>_{amp} - <V_p>_{amp}$, is proportional to $2\alpha_{CW}(T)I_o(T)$ for the polarizing beam splitter 16 axis set to 45° to that of the polarization of the light source 20 and the sum of the amplitudes, $<V_s>_{amp} + <V_p>_{amp}$ is proportional to $I_o(T)$, the intensity of the collimated output beam 25.

Another type of the CW polarimeter/interferometer is an instrument configured as two independent polarization sensitive interferometers operating in the right(R) and left(L) circular polarization basis, yielding the two phase measurements $\phi_R(T)$ and $\phi_L(T)$. In this case, the sum $(\phi_R + \phi_L)$ is proportional to $\phi_{CW}(T)$ and the difference $(\phi_R - \phi_L)$ to $\alpha_{CW}(T)$. This illustrates that plasma polarimetry is, intrinsically, an interference effect and polarization sensitive interferometry is sufficient to measure both a chord averaged $n_e$ and chord averaged $n_e B_\parallel$ product.

The CW plasma polarimeter uses a continuous linearly polarized light source of determined wavelength, $\lambda_o$, but the light source need not be coherent. The Faraday effect causes a progressive rotation in the polarization of the probe beam as it propagates in the magnetized plasma in the linear polarization basis. In a circularly polarized ("helicity") basis, the Faraday effect can be viewed as a progressively increasing difference in phase between two coherent probe beams, one left circularly polarized, the other right. The two pictures can be reconciled by noting that a linearly polarized light source is the superposition of equal amplitudes of left and right circularly polarized light. In essence, the magneto-optic Faraday effect is an interference phenomenon between two coincident probe beams, one left, the other right circularly polarized, both naturally provided by a linearly polarized light source. The rotation angle, $\alpha_{CW}$, is the interference (difference in phase) between the two probe beams. The difference phase for two probe beams with the same beam path is immune to common mode phase (coherence) effects. A linearly polarized incoherent light source is sufficient for polarimetry because the necessary interfering components in the helicity basis are all naturally present in the right proportions.

The difference phase, $\alpha_{CW}$, also lies in an orthogonal space (the plane of polarization) to that of the temporal phase. The $\lambda_o$ dependence is the only connection between the temporal properties of the light source with rotation angle, $\alpha_{CW}$.

The CW plasma interferometer measures the difference in phase between the temporal phase of the scene beam and the reference beam at the optical detector. The phase measurement is subject to coherence effects since these two beams have different beam paths. The phase measurement is directly affected by the phase noise of the light source and phase noise introduced to either beam in such a way that is not common to both beams.

Another remote sensing, non-perturbative diagnostic in this field is the Thomson scattering LIDAR(LIght Detection and Ranging) instrument but this diagnostic does not exploit the polarization of the light source or contribute to the remote sensing of the magnetic field. A LIDAR Thomson scattering instrument is employed on the JET tokamak to measure the local electron density distribution, $n_e(s)$, and the local electron temperature distribution, $T_e(s)$, from the intensity and spectral distribution, respectively, of backscattered light induced by a propagating light pulse in the plasma along the light pulse beam path. The location of the measurements are given by time-of-flight and the spatial resolution is determined by the light pulse length and the response time of the optical detector. The instrument is ideal for remote sensing of $n_e(s)$ and $T_e(s)$ in future devices.

SUMMARY

Various embodiments of the present invention are directed to pulsed polarimeters that can be used for conducting remote, non-perturbative diagnostic measurements of inducing fields of a medium demonstrating induced optical activity. In one aspect of the present invention, a pulse polarimeter comprises a light source and a light gathering optical system. The light source is configured to emit a polarized light pulse having sufficiently narrow spatial extent and at a prescribed wavelength, and the light gathering optical system includes a light gathering optic having a optic axis directed toward the medium and positioned so that a predetermined solid angle of an emission from the medium is collected and collimated into a collimated emission beam, wherein the light gathering optic preserves the polarization state of the emission. The pulse polarimeter also includes a directional coupler and a polarization detection system. The directional coupler is configured to make coincident the propagation direction of the polarized light pulse with the optic axis of the light gathering optic and direct the polarized light pulse toward the medium. The polarization detection system is configured to measure the intensity and determine the polarization state of the collimated emission beam continuously in time as the polarized light pulse transits the medium, wherein the intensity and polarization state can be used to determine the inducing fields.

DRAWINGS

Reference Numerals

Figure 1:
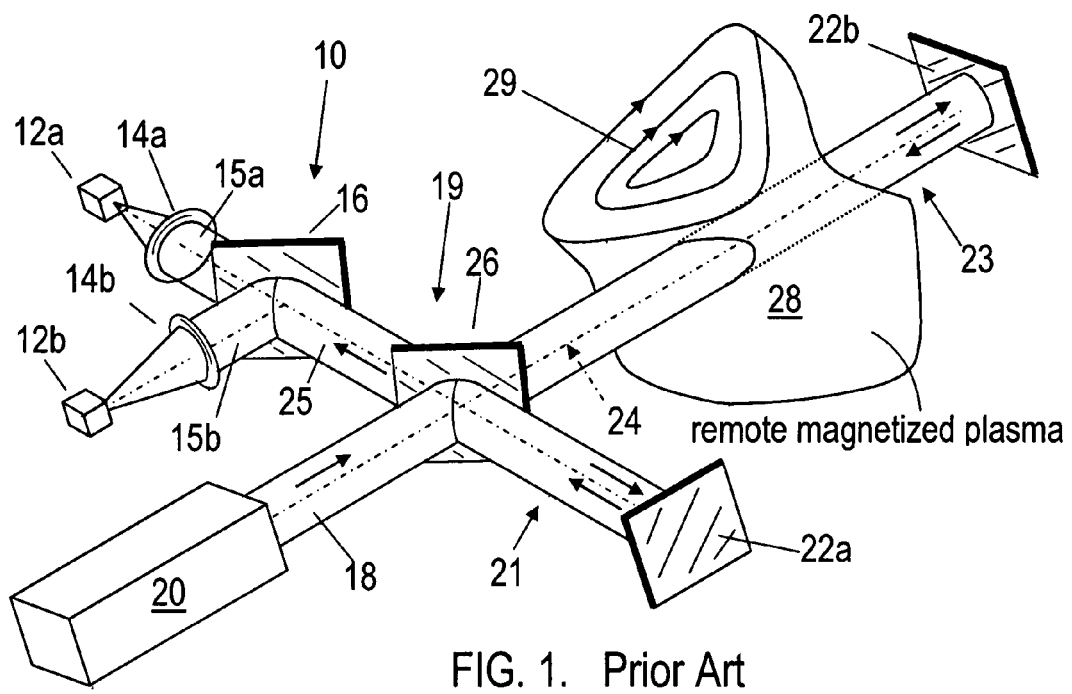
FIG. 1 shows a schematic representation of a perspective view of a continuous wave polarimeter/interferometer.
Figure 2A:
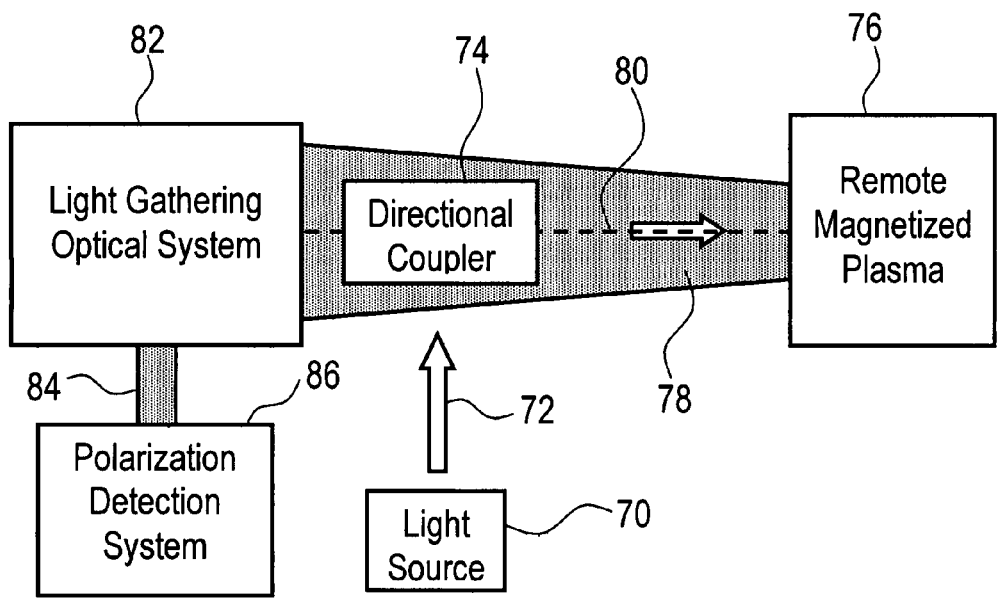
FIG. 2A shows a schematic representation of a pulsed polarimeter in accordance with embodiments of the present invention.
Figure 2B:
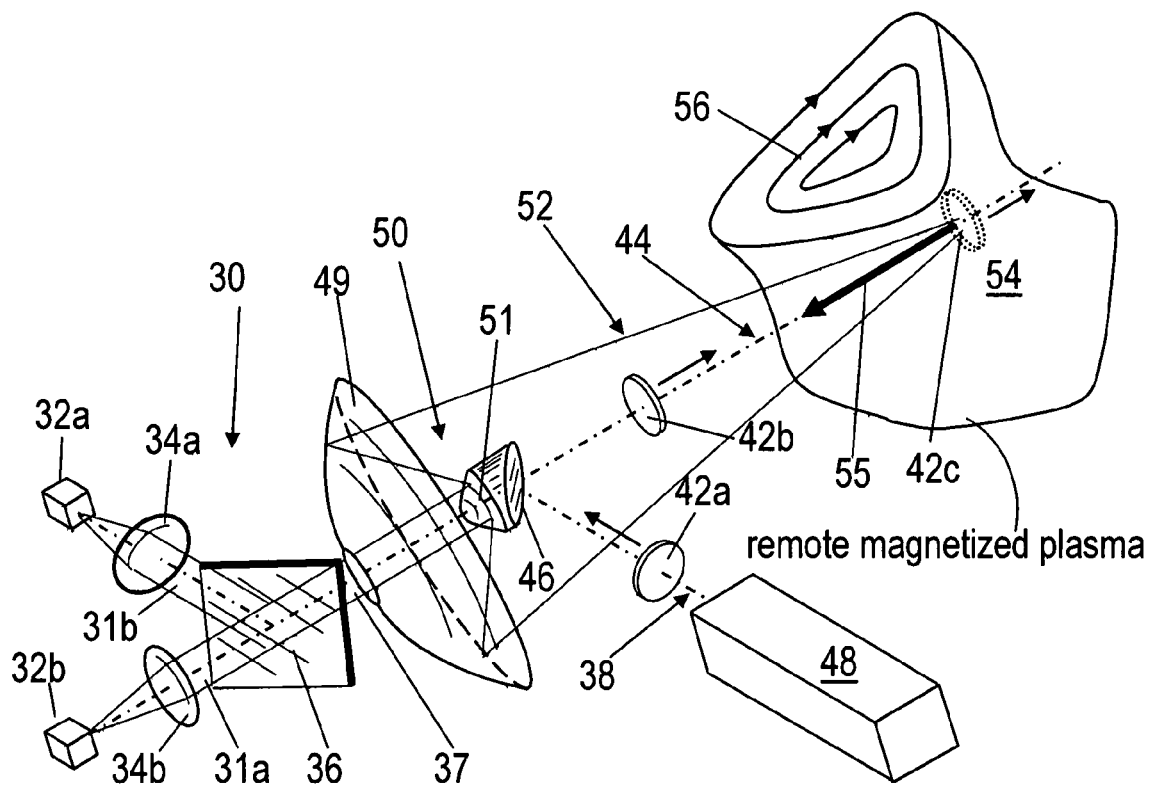
FIG. 2B shows a perspective view of components of a pulsed polarimeter in accordance with embodiments of the present invention.
Figure 3:
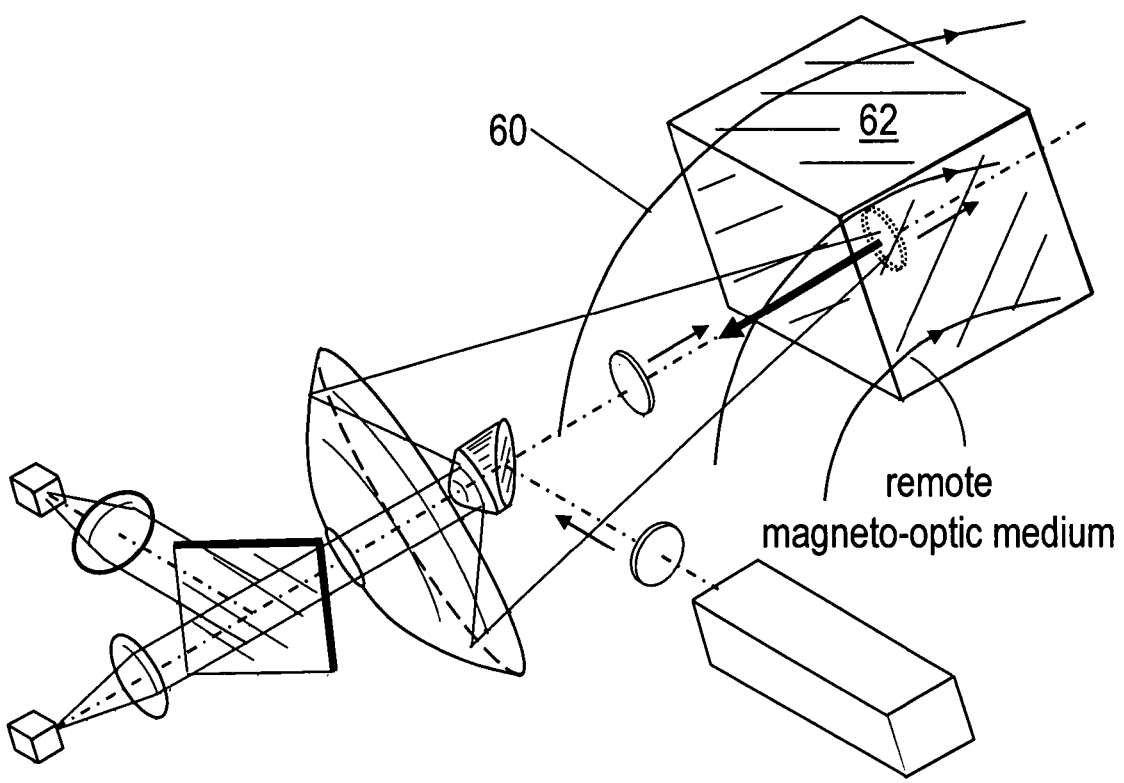
FIG. 3 shows a schematic representation of a perspective view of a second pulsed polarimeter in accordance with embodiments of the present invention.
Figure 4A:
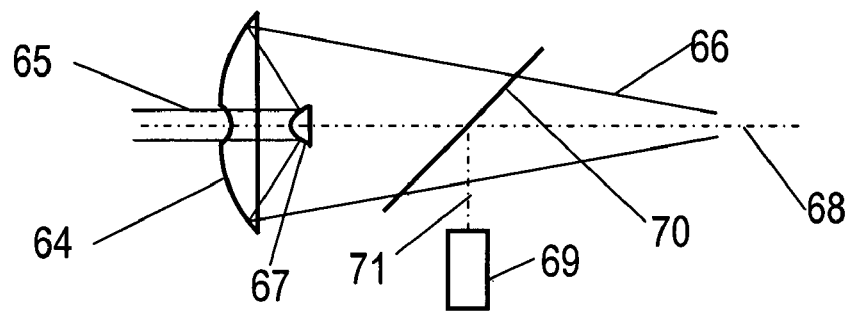
FIGS. 4*a*-4*d* show schematic representations of four different light gathering optical systems, each schematic representation in accordance with embodiments of the present invention.
Figure 4B:
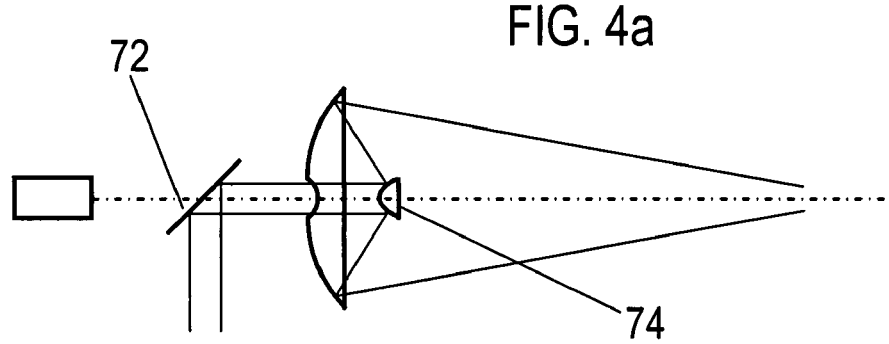
Figure 4C:
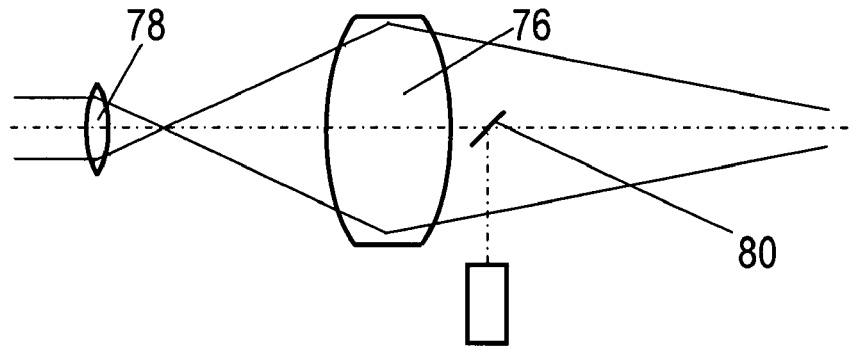
Figure 4D:
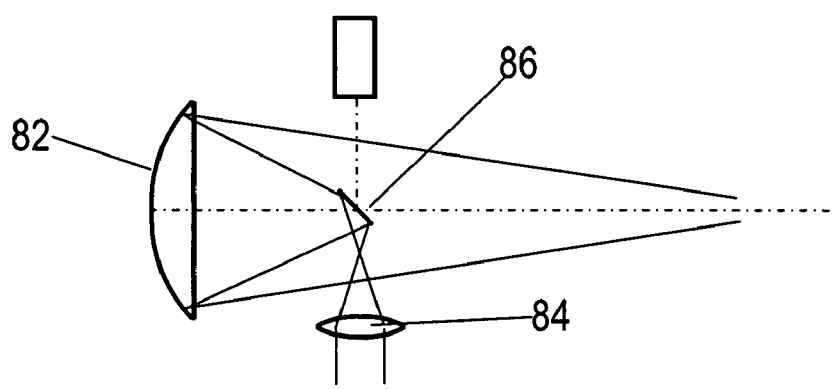

| FIG. 1 Prior Art | | | |
|---|---|---|---|
| 10 | polarization detection system | 12a, b | optical detector |
| 14a, b | focusing lens | 15a, b | collimated analyzed output beam |
| 16 | polarizing beam splitter | 18 | polarized collimated beam |
| 19 | interferometer | 20 | light source |
| 21 | reference beam | 22a, b | end mirror |
| 23 | scene beam | 24 | beam axis |
| 25 | collimated output beam | 26 | directional coupler |
| 28 | remote magnetized plasma | 29 | magnetic field distribution |
| FIG. 2A | | | |
| 90 | light source | 91 | polarized light pulse |
| 92 | directional coupler | 93 | light pulse induced emission |
| 94 | remote optically active medium | 95 | optic axis |
| 96 | light gathering optical system | 97 | collimated emission beam |
| 98 | polarization detection system | | |
| FIG. 2B | | | |
| 30 | polarization detection system | 31a, b | collimated polarized beam |
| 32a, b | optical detector | 34a, b | focusing lens |
| 36 | polarizing beam splitter | 37 | collimated emission beam |
| 38 | propagation path | 42a, b, c | polarized light pulse |
| 44 | optic axis | 46 | directional coupler |
| 48 | light source | 49 | light gathering optic |
| 50 | light gathering optical system | 51 | collimating optic |
| 52 | solid angle | 54 | remote magnetized plasma |
| 55 | light pulse induced emission | 56 | magnetic field distribution |
| FIG. 3 | | | |
| 60 | magnetic field distribution | 62 | remote magneto-optic medium |
| FIG. 4a | | | |
| 64 | light gathering optic | 65 | collimated emission beam |
| 66 | solid angle | 67 | collimating optic |
| 68 | optic axis | 69 | light source |
| -continued | | | |
| 70 | directional coupler | 71 | propagation path |
| | | FIG. 4b | |
| 72 | directional coupler | 74 | collimating optic |
| | | FIG. 4c | |
| 76 | light gathering optic | 78 | collimating optic |
| 80 | directional coupler | | |
| | | FIG. 4d | |
| 82 | light gathering optic | 84 | collimating optic |
| 86 | directional coupler | | |

DETAILED DESCRIPTION

Various embodiments of the present invention are directed to devices and method for determining, at a distance, the distribution of an inducing field associated with a medium demonstrating induced optical activity to a prescribed spatial resolution and accuracy without perturbing the medium. The medium can be a magnetized plasma, a magneto-optic medium, or an electro-optic medium and the inducing field can be a magnetic field or an electric field. A medium demonstrates induced optical activity when a birefringence is induced by the presence of a magnetic field or electric field in the medium, producing a measurable effect on the transmission of polarized light in the medium. Embodiments of the present invention rely on a spatially narrow powerful polarized light pulse from a light source to produce optical emission in the medium. The light pulse induced emission in the backward direction (backscatter) is collected and collimated onto an optical detection system. The polarization state of the collected backscattered emission can be analyzed using a polarimeter (ellipsometer) and the intensity can be measured using a calibrated optical detector. The measurements of the polarization state and intensity, measured continuously in time as the light pulse transits the medium, are used to infer the local strength of the inducing field and electron density along the trajectory of the light pulse in the medium. The location of the measurements is given by time-of-flight. The spatial resolution of the magnetic field and density distributions can be determined by the length of the light pulse and the time resolution of the optical detector. The measurement of the inducing field along the trajectory of the light pulse can be obtained remotely from the medium without the introduction of any foreign material into the medium other than the light pulse itself.

Method embodiments of the present invention are subsequently referred to as pulsed polarimetry and device embodiments of the invention are referred to as a pulsed polarimeter. In the various embodiments of the present invention described below, a number of structurally similar components comprising the same materials have been identified by the same reference numerals and, in the interest of brevity, an explanation of their structure and function is not repeated.

FIG. 2A shows a schematic representation of a pulsed polarimeter in accordance with embodiments of the present invention. The pulsed polarimeter includes a light source 90, a directional coupler 92, a light gathering optical system 96, and a polarization detection system 98. The pulsed polarimeter shown in FIG. 2A represents one of many configuration embodiments of the present invention that can be used to perform a remote, non-perturbative, local measurement of the inducing field in a remote optically active medium 94. The light source 90 emits an intense, polarized light pulse 91 of a sufficiently narrow spatial extent at a prescribed wavelength to the directional coupler 92. The directional coupler 92 is configured to make coincident the propagation path of the polarized light pulse with the optic axis 95 of the light gathering optical system 96 and direct the polarized light pulse toward the remote optically active medium 94, which, in turn, induces a light pulse induced emission 93, backscattered toward the light gathering optical system 96. The light gathering optical system 96 collimates the light pulsed induced emission 93 into a collimated emission beam 97 while preserving the polarization state of the light pulsed induced emission 93 and directs the collimated emission beam 97 to the polarization detection system 98. Based on the polarization state and intensity of the collimated emission beam 97 determined by the polarization detection system 98 as the light pulse transits the remote optically active medium 94, the magnetic field in the remote optically active medium can be assessed along the trajectory of the light pulse in the medium.

FIG. 2B shows a perspective view of components of a pulsed polarimeter in accordance with embodiments of the present invention. As shown in FIG. 2B, a light source 48 can be a laser that emits an intense, linearly polarized light pulse 42a,b,c of sufficiently narrow spatial extent at a prescribed wavelength. The polarized light pulse 42a is emitted from the light source 48 along its propagation path 38 and can be steered by a directional coupler 46 to coincide with an optic axis 44 of a light gathering optic 49 of a light gathering optical system 50. The directional coupler 46 can be a plane mirror. The light gathering optical system 50 includes the light gathering optic 49 and a collimating optic 51. The light gathering optic 49 collects a prescribed finite solid angle 52 of light pulse induced emission 55, also called "backscatter," from a remote magnetized plasma 54 and focuses the emission onto the collimating optic 51. The collimating optic 51 produces a highly collimated emission beam 37 that is transmitted through a hole in the light gathering optic 49 toward a polarization detection system 30. The light gathering optical system 50 continuously images the propagating polarized light pulse 42c along its trajectory in the remote magnetized plasma 54 and, importantly, preserves the polarization state of the light pulse induced emission 55 as the polarization state of the collimated emission beam 37. The optic axis 44 can be aimed to intersect the remote magnetized plasma 54 with a pulse trajectory along which a magnetic field distribution 56 is to be determined. The polarization detection system 30 includes a polarizing beam splitter 36, focusing lenses 34a,b, and optical detectors 32a,b. The polarization state and intensity of the collimated emission beam 37 is determined using the polarization detection system 30 continuously over the transit time of the polarized light pulse 42c in remote magnetized plasma 54. The polarizing beam splitter 36 spatially separates the collimated emission beam 37 into two mutually orthogonal linearly polarized collimated polarized beams 31a,b. Focusing lenses 34a,b condense the collimated polarized beams 31a,b onto the optical detectors 32a,b producing an electrical signal (voltage or current) proportional to the intensity of their respective polarization channels.

Theory Supporting Embodiments of the Present Invention

The operation of embodiments of the present invention for the remote, non-perturbative local measurement of the magnetic field in a magneto-optically active medium proceeds from combining attributes of two physical phenomena that are quite generally present in many optically transmissive media. The two phenomena and their associated attributes are:

I) Light Propagating in a Medium Induces Optical Scattering.

Attribute of I) Optical backscatter induced by a probe beam at a given location in the medium is identical in nature to that produced by a partial retro-reflection of the probe beam by a plane mirror at that location along the propagation path. More to the point, induced optical backscatter inherits the polarization of the inducing probe beam.

II) The Magneto-Optic Faraday Effect is Generally Manifested by Nearly all Media.

Attribute of II) The Faraday effect is non-reciprocal implying that the sense of rotation of the polarization of light propagating in the medium is independent of the direction of propagation.

These are the two key properties that allow the prior art to be generalized with respect to embodiments of the present invention. Taken alone, the two physical phenomena and their attributes seem like innocuous properties of optically transparent media but when combined form a powerful diagnostic tool. These physical principles will now be elucidated and used to explain the operation of embodiments of the present invention.

The Faraday Effect

The Faraday effect denotes a circular birefringence induced by a magnetic field, B, in the magnetized medium—where the characteristic modes of the magnetized medium become the left and right circularly polarized states with differing refractive indices. The magnetic field gives preference to one handedness over the other due to the electrons gyrating about B. The difference in refractive indices sets the strength of the Faraday effect which is proportional to $B_\parallel(B\cdot\hat{s})$, the projection of the magnetic field onto the propagation direction, $\hat{s}$, of the probe beam. A linearly polarized probe beam is the superposition of the two circularly polarized probe beams (characteristic modes) with equal amplitude. As these two modes propagate an incremental distance, ds, in the magnetized medium, an incremental relative phase delay between these modes results, producing an incremental rotation, $d\alpha$, in the plane of polarization of the probe beam in the linear polarization basis.

The Faraday effect is non-reciprocal. A retro-reflection of the probe beam by a plane mirror as with the end mirror 22b retro-reflecting the scene beam 23 of FIG. 1, interchanges the circularly polarized states which would undo the rotation on the reflected path if the orientation of the magnetic field with respect to the reflected beam were not also reversed. The combination of mode interchange and field reversal maintains the same sense of rotation for the reflected path as for the forward path.

The Faraday effect is present in many optically transmissive media and is quantified by V, the Verdet optical constant. The Verdet constant can be as high as 100 rad/T-m for special magneto-optic materials such as Faraday rotator glass. For a magnetized plasma, the Faraday effect is not constant but is proportional to the $n_e$ and B distributions as given by:

$$\alpha(l, T) = 2.63 \times 10^{-13} \lambda_o^2 \int_0^l (n_e B_\parallel)(s, t(s))\, ds \qquad \text{Eq. 3}$$

for a probe beam propagating in the magnetized plasma. Eq. 3 can be interpreted as before: the polarization of the probe beam rotates an angle $\alpha(l,T)$ in the plane of polarization as the probe beam propagates along a path parameterized by path length, s, from the plasma edge (s=0) to a location, s=l, in the magnetized plasma proportionally to the line integrated $n_e B_\parallel$ product along the path. The time, T, is identified with the entire path integral, a duration of l/c seconds. The time along the path is given by t(s)=s/c. The proportionality constant has a strong quadratic dependence on the wavelength of the light source, $\lambda_o$. The prior art CW polarimeter measures $\alpha(L_p,T)$ for a single pass and $2\alpha(L_p,T)$ for the double pass according to attribute of II). This formula is valid if the frequency of the light is far above any cutoff frequency along the path. $n_e$ and $B_\parallel$ are generally time dependent but assumed constant ("quasi-static") on a time scale of l/c. In this case, t(s) can be replaced by T in Eq. 3.

Eq. 3 differs from Eq. 1 in that the path integral stops at an interior location $l(<L_p)$ of the magnetized plasma. This is achieved in the present invention by propagating a spatially localized polarized light pulse through the plasma with sufficient intensity to induce a measurable amount of emission at location l. Sensing properties of the optical emission induced by the light pulse within the plasma as opposed to sensing properties of the light itself, as in the prior art CW plasma polarimeter, has profound implications. For one, the sensed property is localized to a location inside the plasma, in this case, $\alpha(l,T)$, as a path integral up to location l. Second, a signal is only present when the light pulse is in the medium and is stronger at locations with higher local density as opposed to the prior art CW polarimeter where the intensity of the beam is constant whether or not a plasma is present. It is this second property that allows a simultaneous determination of the local density at location l of the plasma. The pulsed polarimeter makes the most efficient use of the polarization detection system by spatially resolving both the rotation angle and plasma density.

Figure 5:
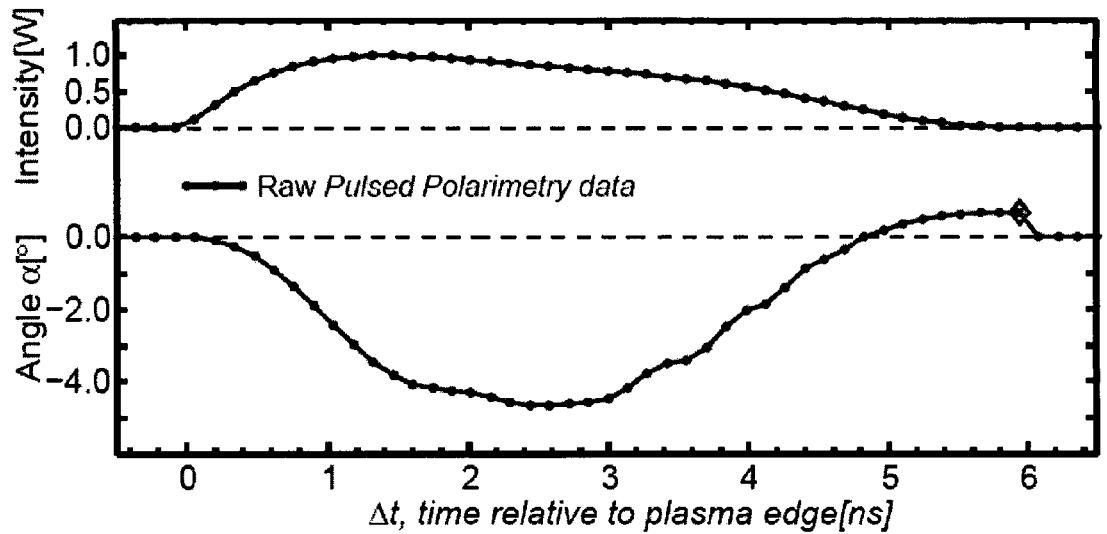
FIG. 5 shows an illustration of the pulsed polarimeter measurements of local intensity and local rotation angle as sampled data in time in accordance with embodiments of the present invention.

It is not at all evident that the induced optical scatter from the polarized light pulse can provide the necessary details of the polarization state of the polarized light pulse at location l. But, for scattering in the backward direction (backscatter) it is the case. The pulsed polarimeter measures the polarization of the backscattered light induced by the polarized light pulse as it propagates along its trajectory through the plasma. Invoking the attribute of I), the backscattered light inherits its polarization direction from the polarization of the polarized light pulse at location l, $\alpha(l,T)$, as given by Eq. 3. The backscattered light approximately retraces the beam trajectory acquiring an additional rotation angle $\alpha_r(l,T)$ according to the attribute of II), the subscript r denotes a reversal of direction. If the magnetic field and density are quasi-static on a 2l/c time scale, then $\alpha_r(l,T)=\alpha(l,T)$ and the pulsed polarimeter measurement is $2\alpha(l,T)$. The time, T, is identified with both path integrals, a duration of 2l/c seconds. An illustration of a time trace of rotation angle Vs the delay time relative to the plasma edge, $\Delta t$, for a pulsed polarimeter is shown in FIG. 5. The diamond point on the trace corresponds to the light pulse positioned at the plasma edge ($s=L_p$) and corresponds with the one and only measurement of the prior art CW plasma polarimeter, $2\alpha(L_p,T)=\alpha_{CW}(L_p,T)$. The delay time scale, $\Delta t$, can be converted to a distance scale, $l=c\Delta t/2$, from the edge of the plasma noting that backscatter at the far edge, induced at time $L_p/c$, takes an additional $L_p/c$ seconds to arrive at the detector or $2L_p/c$ total. The transit time, $2L_p/c$, is so short (6.6 ns/m) that the magnetic field and density profiles can be assumed quasi-static for most applications. The quasi-static assumption is also a basic assumption of the prior art CW polarimeter/interferometer instrument.

The rotation angle formula, Eq. 3, can be solved for the $n_e B_\parallel(l)$ product profile at time T and is given by:

$$n_e B_\parallel(l,T) = \frac{1.9 \times 10^{12}}{\lambda_o^2} \left(\frac{d\alpha(s,T)}{ds}\right)\bigg|_l \qquad \text{Eq. 4}$$

The desired local quantity $n_e B_\parallel(l,T)$ is proportional to the differential change of $\alpha$, $d\alpha$, per differential change in path length, ds, which encapsulates the magneto-optic Faraday effect with regards to pulsed polarimetry. One way to view the result is that the rotation angle trace, $\alpha(l,T)$, has been dissected or partitioned into pieces, an incremental rotation angle, $\Delta\alpha(l,T)=5.26\times10^{-13}\lambda_o^2 n_e B_\parallel(l,T)\Delta s$ for an incremental path length, $\Delta s$, and each piece is proportional to local $n_e B_\parallel(l,T)$. It is more correct to view the measurement of, $\Delta\alpha(l,T)$ or $n_e B_\parallel(l,T)$, as the difference of two non-local double-pass path integrals over the magnetized plasma from s=0 to l and s=0 to l+$\Delta s$, separated by 2$\Delta s$/c seconds.

Scattering

Light propagating in a medium induces scattered light. The scatter is radiation from electrons (ions contribute negligibly) accelerated by the electric field of the light. If the electron positions are correlated, the scattering intensity can be strong (coherent scattering, diffraction). Uncorrelated (random) electron positions produce weak but non-zero scattering intensity (incoherent scattering) due to the discrete particle nature of the electrons. The intensity of incoherent scattering is proportional to $n_e$.

For plasmas, Thomson scattering is a familiar scattering process and is the scattering mechanism of the embodiment of FIG. 2B. Thomson scattering is radiation from unbound electrons accelerated by the electric field of the probe beam. For relatively low temperature plasmas ($T_e<10$ million° C. or 1 keV) where relativistic effects can be neglected, the accelerated electrons produce a dipole radiation pattern. The electric field amplitude of dipole radiation, $E_s$, for an arbitrary direction, $\hat{R}$, and $E_{bs}$ for the backward direction, $\hat{R}=-\hat{s}$, is given by:

$$E_s = -\frac{r_e}{(R+l)}\hat{R}\times(\hat{R}\times E_i) \qquad \text{Eq. 5}$$

or $$E_{bs} = -\frac{r_e}{(R+l)}E_i \text{ for } (\hat{R}=-\hat{s})$$

where $\hat{s}$ is the propagation direction of the probe beam. The backscatter electric field amplitude, $E_{bs}$, is seen to be aligned (anti-parallel) with the inducing electric field, $E_i$, falls off with distance, (R+l), to the sensing instrument and is attenuated by a factor $r_e$, the classical electron radius ($2.82\times10^{-15}$ m), identical to the electric field amplitude retro-reflected from a weak plane mirror at location, (R+l).

The total scattered electric field amplitude is the sum of all individual dipole fields in the scattering volume. The polarization of the sum maintains its alignment to $E_i$, since each individual dipole is aligned. Thomson scattering can be coherent or incoherent. For the embodiment shown in FIG. 2B, the Thomson scattering regime is incoherent with scattered intensity directly proportional to the density of scatterers, $n_e$. For coherent scattering, a correspondence between the scattered intensity and electron density would need to be established.

For high temperature plasmas ($T_e$>1 keV), relativistic effects depolarize the scattered radiation to some degree. However, in the backward direction the depolarizing effect is zero and near zero for a wide angular range around the backward direction. Thus attribute of I) holds for all magnetized plasmas at any temperature.

Optical scattering in any medium arises in the same way as described for plasmas, as radiation from electrons accelerated by the incident electric field of the probe beam and the backscatter quite generally inherits the polarization of the inducing light in the scattering volume.

Operation and Other Pulsed Polarimeter Embodiments

Referring again to FIG. 2B, a pulsed polarimeter is composed of four main elements. 1) The light source 48 which emits a spatially narrow polarized light pulse 42a of determined wavelength. The polarized light pulse 42c in the remote magnetized plasma 54 produces light pulsed induced emission 55 or optical emission in the backward direction (backscatter). 2) The light gathering optical system 50 which collects a determined solid angle 52 of light pulse induced emission 55 and produces a collimated emission beam 37. The light gathering optical system, importantly, preserves the polarization state of the collected light pulse induced emission. The light gathering optical system 50 includes the light gathering optic 49 with the optic axis 44 and the collimating optic 51. 3) The directional coupler 46 which makes coincident the light pulse propagation path 38 and the optic axis 44 to ensure that backscatter is collected and that the polarized light pulse 42c is imaged along its entire trajectory in the plasma. And 4) the polarization detection system 30 which measures the intensity and determines the polarization state of the collimated emission beam 37 and thereby, the polarization state of the light pulse induced emission 55. The polarization detection system 30 includes the polarizing beam splitter 36 which analyzes and spatially separates the collimated emission beam 37 into two mutually orthogonal collimated polarized beams 31a,b, the focusing lenses 34a,b which focus the collimated polarized beams 31a,b onto the optical detectors 32a,b producing electrical signals proportional to the intensity of the collimated polarized beams 31a, b. The magnetic field and density profiles are determined from the continuous measurements of intensity and polarization state. The location of the measurements are given by time-of-flight, $l=c\Delta t/2$, and spatial resolution is determined by the length of the polarized light pulse and the response time of the optical detectors 32a,b.

1) The Light Source

In other embodiments of the present invention, the light source 48, shown in FIG. 2B, can be a laser that emits a linearly polarized, intense, spatially narrow polarized light pulse 42a. The pulse duration, pulse length, pulse energy, beam radius, beam area and wavelength are denoted by $\tau_{pulse}$, $L_{pulse}(c\tau_{pulse})$, $E_{pulse}$, $r_{beam}$, $A_{beam}(\pi r_{beam}^2)$ and $\lambda_o$. The wavelength, $\lambda_o$, can be chosen to set the strength of the Faraday effect. If the Faraday effect is too strong the characteristic modes may separate spatially. The choice of $\lambda_o$, is determined with the application in mind but a wavelength that produces an $\alpha(L_p)$ of 0.5(30°) is considered generally appropriate. The laser frequency can be chosen to be above the cutoff frequency which is density dependent and varies along the trajectory as $v_{cutoff}=9\sqrt{n_e(s)}$. The scattering can be placed in the incoherent regime by reducing the wavelength below a level that is both temperature and density dependent: $\lambda_o<870\sqrt{(T_e/n_e(s))}$. The coherence properties of the light source 48 do not play a role in this embodiment of the pulsed polarimeter. The spectral width, $\Delta\lambda$, of a pulsed light source is given by $\lambda_o^2/L_{pulse}$. A shorter pulse length produces a greater spectral width.

There are various possibilities with regards to the light source 48 and the types of light emitted from the light source 48. For example, in other embodiments, light emitted from the light source 48 can be right or left circularly polarized or in general, elliptically polarized and the light source 48 can be coherent in order to be used in combination with a phase-sensitive polarization detection system 30. The pulsed nature of pulsed polarimetry further allows more general schemes for the light source 48 over that of CW plasma polarimetry: the polarized light pulse 41a emitted from the light source 48 can be frequency modulated or chirped in frequency, for instance, to profile the wavelength of the light pulse. The light source 48 can also be an incoherent light source producing an intense, spatially narrow pulse of incoherent polarized light. In addition, several independent light sources can be combined. For instance, the polarized light pulses from two light sources of different wavelengths can be combined, or two polarized light pulses in different polarized states, say left circularly polarized and right circularly polarized, can be combined into one polarized light pulse.

2) The Light Gathering Optical System

The light gathering optical system 50 collects and collimates the light pulse induced emission 55 or backscatter from the polarized light pulse 42c propagating in the remote magnetized plasma 54. The solid angle 52, $\Delta\Omega$, with cone angle, $\theta_{\Delta\Omega}$, of the light pulse induced emission 55 is collected using a light gathering optic 49. The light gathering optic 49 could also collimate the collected emission but would in general, produce a collimated emission beam 37 with a beam diameter that would be too large. A second optical element, the collimating optic 51, is used to receive focused light from the light gathering optic 49 and produce a collimated emission beam 37. Importantly, the light gathering optical system 50 has a cross polar coupling that is nearly net zero. In other words, polarization is preserved by light gathering optical system 50 so that the polarization state of the collimated emission beam 37 is the same polarization state as the light pulse induced emission 55 in an average sense. The light gathering optical system 50 can introduce parasitic polarized light orthogonal to the polarization of the light pulse induced emission 55 as long as the parasitic polarized light component averages to zero over the aperture of the collimated emission beam 37. In the embodiment shown in FIG. 2B, cylindrical symmetry about the optic axis 44 is maintained by the reflective surfaces of the light gathering optic 49 and the collimating optic 51 to yield a net zero cross polar coupling. In general, curved reflecting surfaces that are mirror symmetric about a plane containing the optic axis 44, yield net zero cross polar coupling. The angular departure, $\gamma_{coll}$, from a perfectly collimated emission beam 37 is given by the ratio of the radius, $r_{beam}$, of the imaged portion of the polarized light pulse 42c to the image distance R+l, $r_{image}/(R+l)$, and is on the order of 1 arc minute for R=3 m and $r_{image}$=1 mm. In practice, the light source 48 would be collimated or focused so that $r_{beam}<r_{image}$. The etendue of the light gathering optic system 50 is $\pi r_{image}^2\Delta\Omega$ or $\pi r_{beam}^2\Delta\Omega$ for $r_{beam}<r_{image}$. In other embodiments of the present invention, there are various possibilities with regards to the kinds of devices that can be used to implement the light gathering optical system 50 as shown in FIGS. 4a,b,c,d. In FIG. 4a, similar to FIG. 2B, are shown a light source 69 with a propagation path 71, a light gathering optic 64, a collimating optic 67, an optic axis 68, a solid angle 66 and a collimated emission beam 65. Lenses (refracting optics) can be substituted for both of the light gathering optic 76 and the collimating optic 78 as shown in FIG. 4c or a mixture of lenses and reflectors can be used as in FIG. 4d where a collimating optic 84 is a lens and a light gathering optic 82 is a reflector, in this case without a hole. Off-axis reflectors (off-axis ellipsoids) can also be used to focus the emission off axis. Two optical components allow a wide choice of optics that can be matched to be polarization preserving.

3) The Directional Coupler

The directional coupler 46 in the embodiment shown in FIG. 2B can be a plane mirror attached to the back surface of the collimating optic 51. The directional coupler 46 makes coincident the pulse propagation path 38 with the optic axis 44 of the light gathering optic 49 and directs the polarized light pulse 42b toward the remote magnetized plasma. The propagation path 38 is made coincident with the optic axis 44 on the surface of the directional coupler 46 which is steered to bring about a coincidence in direction. In other embodiments of the present invention, there are various possibilities with regards to the kinds of devices that can be used to implement the directional coupler 46 as shown in FIGS. 4a,b,c,d. As shown in FIG. 4a, a directional coupler 70 spans the entire solid angle 66 and could be a non-polarizing beam splitter or a frequency selective reflector. A non-polarizing beam splitter directional coupler 70 is less efficient as it is not 100% reflecting for the light source 69 or 100% transmitting for the collected emission. FIG. 4b illustrates a directional coupler scheme with the light source directly behind the light gathering optic with the light pulse propagation beam and optic axis aligned. The directional coupler 72 is again a non-polarizing beam splitter, a frequency selective reflector or a plane mirror with a hole along the optic axis to allow the light pulse to pass through. The collimating optic 74 must also have a hole to allow the light pulse to pass through. In FIG. 4c a directional coupler 80 is a small plane mirror reflector between the pulsed polarimeter and the medium. The embodiment shown in FIG. 4d similarly uses a plane mirror directional coupler 86 to direct the light pulse along the optic axis and to steer the emission toward the collimating optic 84, a lens. FIGS. 4a-4b show only four embodiments and are by no means intended to be exhaustive of the kinds of devices that can be used to implement the directional coupler 46. Other kinds of devices and arrangements of these devices can be used to implement the directional coupler 46 which are also consistent with embodiments of the present invention.

4) The Polarization Detection System

The polarization detection system 30 in the embodiment shown in FIG. 2B uses the polarizing beam splitter 36 configured to spatially separate the collimated emission beam 37 output from the light gathering optical system 50 into two mutually orthogonal linearly polarized collimated polarized beams 31a,b. The ability of the polarizing beam splitter 36 to adequately separate the two polarization states of the single collimated emission beam 37 is dependent on the quality of the polarizer and on the angle $\gamma_{coll}$, which quantifies the departure of the collimated emission beam 37 from perfect collimation. The two collimated polarized beams 31a,b are focused with focusing lenses 34a,b onto optical detectors 32a,b. The solid angle, $\Delta\Omega_{pol}$, of the focusing lenses 34a,b can be determined by matching the etendue of the light gathering optic 49, $A_{beam}\Delta\Omega$, to that of the etendue of the focusing lens, $A_{det}\Delta\Omega_{pol}$, where $A_{det}$ is the area of the optical detector. Setting $A_{beam}\Delta\Omega$ equal to $A_{det}\Delta\Omega_{pol}$ optimally couples the collected backscatter 55 to the optical detectors 32a,b. The optical detectors 32a,b use direct detection to produce an electrical output (voltage or current), proportional to the intensity of the collimated polarized beams 31a,b. The optical detectors 32a,b can be calibrated to measure absolute intensity. The calibration includes the optical detector's responsivity (R) and quantum efficiency ("QE") ($\eta$), both of which are usually wavelength dependent. The bandwidth of the optical detectors, $BW_{det}$, is typically several GHz requiring small $A_{det}$, on the order of 0.01 mm$^2$ for photodiode detectors.

If the axis of the polarizing beam splitter 36 is aligned with the polarization of the light source 48, the weak detector channel will be proportional to $\sin^2(\alpha(l))\sim\alpha(l)^2$, for small $\alpha(l)$, where $l=c\Delta t/2$ for $\Delta t=0$ to $2L_p/c$. T is constant for the profile determination and suppressed. The sensitivity of the polarization detection system 30 can be markedly improved by aligning the axis of the polarizing beam splitter 36 to be 45° to the polarization of the light source 48 and differencing the signals of the two optical detectors 32a,b. For balanced optical detectors 32a,b, $(V_s-V_p)$, is proportional to $I_o(l)(\cos^2(\pi/4+\alpha(l))-\sin^2(\pi/4+\alpha(l)))\sim 2\alpha(l)I_o(l)$, for small $\alpha(l)$. The sum of the voltages, $(V_s+V_p)$, is proportional to $I_o(l)$, the total intensity of the collimated emission beam 37. Demonstrating a much higher sensitivity to $\alpha(l)$ for small $\alpha(l)$. The two measurements allow a determination of $\alpha(l)$ and $I_o(l)$. The polarization detection system 30, described above, can be used with a coherent light source as well as an incoherent light source.

In other embodiments of the present invention, the polarization detection system 30 can be phase-sensitive using optical mixers in place of optical detectors 32a,b together with a coherent light source 48. In such a system, the phase of the polarized light pulse at each location can be determined, the equivalent of an interferometer implementation of a pulsed polarimeter. The optical mixers in such a scheme need an optical local oscillator ("LO"). This can be provided by another coherent laser light source or splitting off some of the coherent polarized light pulse into a reference delay line, a fiber optic for instance, and using the continuous backscatter from the delay line as an LO input to the optical mixer. The mixing can be achieved with a mixing beamsplitter (non-polarizing or polarizing) inserted after the polarizing beam splitter 36 to combine the LO (polarized or non-polarized) with the collimated polarized beam 31a,b as an input to an optical detector. These techniques are known as heterodyne and homodyne detection techniques and have an intrinsic advantage in measurement Signal to Noise Ratio ("SNR") to that of the direct detection SNR. Since the detected intensity is a product of the LO electric field amplitude with the electric field amplitude of the collimated emission beam 37 the signal levels can be boosted significantly by using a strong LO source.

Scattering Details

The polarized light pulse 42c propagating in the remote magnetized plasma 54 induces backscatter 55 from a scattering volume, dV(l), at location l. The length of the scattering volume in the direction of propagation, dL, is given by a familiar LIDAR result:

$$dL=(c\tau_{det}+L_{pulse})/2 \qquad \text{Eq. 6}$$

where $\tau_{det}$ is the integration time of the optical detector. The localization of the backscatter along the trajectory can be as small as $L_{pulse}/2$ or as large as $L_p$ depending on $\tau_{det}$. $dV=\pi r_{beam}^2 dL$.

The intensity, $I_o(l)$, of the collimated emission beam 37 of the collected backscatter 55 from the polarized light pulse 42c at location l is directly related to $n_e(l)$, $\Delta\Omega(l)$, and $E_{pulse}$, given by:

$$I_o(l) = 7.8 \times 10^{-30} E_{pulse} n_e(l) \Delta\Omega(l) \frac{(c\tau_{det} + L_{pulse})}{2\tau_{det}} \quad \text{Eq. 7}$$

The solid angle 52 collected by the light gathering optic 49, $\Delta\Omega(l)$, is a known function of l.

Figure 6:
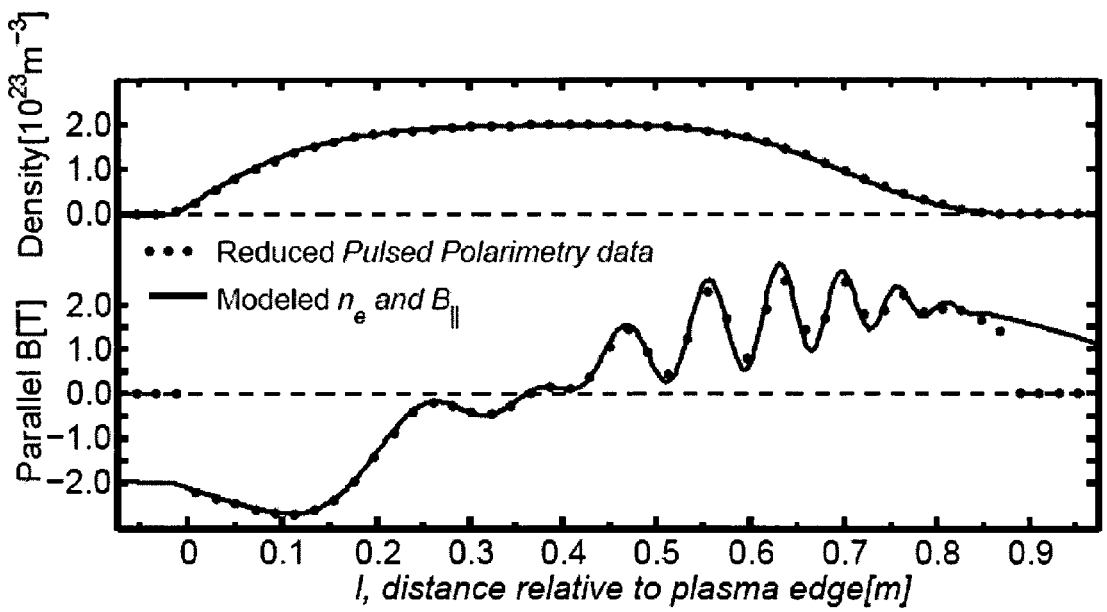
FIG. 6 shows an illustration of the reduced data from the pulsed polarimeter measurements of FIG. 4 as sampled profile measurements of density and magnetic field together with the modeled density and field inputs in accordance with embodiments of the present invention.

An illustration of $I_o$ Vs $\Delta t$ sampled points is shown in FIG. 5. The density profile, $n_e$ Vs l, at sampled points is obtained from Eq. 7 using $l=c\Delta t/2$ and is shown in FIG. 6 along with the modeled density waveform. The intensity profile in FIG. 5 is seen to fall off with, l, or $\Delta t$ since $\Delta\Omega(l)$ decreases with distance. The density profile is obtained by correcting for this geometrical effect and using the known parameters: $E_{pulse}$, $\tau_{det}$ and $L_{pulse}$.

Combining Scattering with the Faraday Effect

The polarization of the polarized light pulse 42c at location l in the remote magnetized plasma 54 has been rotated by $\alpha(l,T)$ in the plane of polarization. The light pulse induced Thomson scattering light pulsed induced emission 55 inherits the polarization of the polarized light pulse according to attribute of I). The backscatter retraces the trajectory acquiring a total rotation angle of $2\alpha(l,T)$ according to attribute of II) for a quasi-static magnetic field and electron density. This is not strictly true as the light pulsed induced emission 55 collected by the light gathering optical system 50 deviates from the backward direction by $\theta_{\Delta\Omega}$. The magnitude of $\Delta\Omega$ is a compromise between a higher signal level (increasing $\Delta\Omega$) and restricting the collected light pulsed induced emission 55 to smaller $\theta_{\Delta\Omega}$, reducing $\Delta\Omega$, but more closely adhering to the principles of pulsed polarimetry. The range of solid angle is determined by the particular application.

Detection and Measurement Process

The optical detectors 32a,b measure intensity using direct detection for the embodiment shown in FIG. 2B, essentially narrowband bolometry. Heterodyne detection can also be used.

The optical detector's response time, $\tau_{det}$, sets the bandwidth, $BW_{det}(=225 \text{ GHz-ps}/\tau_{det})$ ($BW_{det}=2.25$ GHz for $\tau_{det}=100$ ps) of the output signal. The sampling rate must be more than $2BW_{det}$ to avoid aliasing. The $\alpha$ Vs $\Delta t$ and $I_o$ Vs $\Delta t$ traces shown in FIG. 5 illustrate data sampled at a rate of ~7 GS/s with $BW_{det}<3.5$ GHz or $\tau_{det}>75$ ps. The spatial resolution, dL is not specified as it depends on $L_{pulse}$.

The magnetic field, $B_\parallel$, is obtained from the sampled $\alpha_j$ and $n_{ej}$ by:

$$B_{\parallel(2j+1)/2} = \frac{1.9 \times 10^{12}}{\lambda_o^2 (n_{e_{j+1}} + n_{e_j})/2} \left( \frac{\alpha_{j+1} - \alpha_j}{\delta L} \right) \quad \text{Eq. 8}$$

a numerical translation of Eq. 4 where j is the sampling index and $\delta L$ is the distance increment for the time sampled data. The analyzed $B_\parallel$ Vs l trace is shown in FIG. 6 along with the modeled magnetic field. $\delta L$~2 cm, given by the sampling time step $\delta t$~0.14 ns, ($\delta L = c \delta t / 2$).

Localization and Spatial Resolution of the Magnetic Field

The location, l, of the measurement in the medium is given by time-of-flight from the measurement time $\Delta t$, $l=c\Delta t/2$ or $l=c\Delta t/2-R$ including the distance, R, from the light gathering optic 49 to the remote magnetized plasma 54.

The $B_\parallel$, and $n_e$ measurements are spatial averages over the scattering volume, dV. In the trajectory direction, the measurements are spatial averages over dL.

The Magnetic Field Accuracy

The accuracy of the $B_\parallel$, and $n_e$ measurements depends on the measurement SNR which itself depends on many factors: $E_{pulse}$, $\tau_{det}$, $\Delta\Omega$, the background light level, the detector noise level, etc, to be discussed shortly. The range of the pulsed polarimetry technique is affected by the nature of the Faraday effect itself. The rotation angle, $\alpha(l,T)$, given by Eq. 3, is dispersive having a quadratic dependence on $\lambda_o$. Since a light pulse of length, $L_{pulse}$, necessarily has a wavelength spread, $\Delta\lambda$, of $\lambda_o^2/L_{pulse}$, a desired decrease in $L_{pulse}$ only increases $\Delta\lambda$ introducing a wider spread, $\delta\alpha$, in $\alpha$. The measurement error from this effect may be unacceptably high especially at a more desirable higher spatial resolution or lower $L_{pulse}$. $\Delta\lambda$ is considerably reduced by lowering $\lambda_o$ but the strength of the Faraday effect is also lowered. The higher the intrinsic $n_e B_\parallel$ product of the plasma, the lower $\lambda_o$ can be set. For some magnetized plasmas the $n_e B_\parallel$ product may be too low for an accurate local field measurement.

i) Parameter Range of the Pulsed Polarimetry Technique

Given a stationary remote magnetized plasma 54 with uniform electron density, $n_{eo}$, uniform parallel magnetic field, $B_o$, and size $L_p$, a rotation angle wavenumber, $k_\alpha$ and rotation angle wavelength $\lambda_\alpha$ can be defined by:

$$k_\alpha = \frac{d\alpha(l)}{dl} = \frac{2\pi}{\lambda_\alpha} = 2.63 \times 10^{-13} \lambda_o^2 n_{eo} B_o \quad \text{Eq. 9}$$

The wavelength, $\lambda_o$, is chosen so that $\alpha(L_p)$~$0.5(30°)$ or $L_p<\lambda_\alpha$. The Faraday effect is dispersive: $k_\alpha$ depends on $\lambda_o$.

A light pulse of length, $L_{pulse}$, necessarily has a wavelength spread, $\Delta\lambda$~$\lambda_o^2/L_{pulse}$, resulting in a rotation angle spread, $\delta\alpha(l)=(2\Delta\lambda/\lambda_o)\alpha(l)=(2\lambda_o/L_{pulse})k_\alpha l$, increasing linearly with l and attaining a maximum value of $(2\lambda_o/L_{pulse})\alpha(L_p)$ at $L_p$. $N_\lambda=L_{pulse}/\lambda_o$ is the number of wavelengths in a pulse length, $L_{pulse}$. Taking $dL=L_{pulse}=c\tau_{det}$ gives $\Delta\lambda=\lambda_o^2/dL$. The magnetic field measurement is determined by an incremental rotation angle of $\alpha$, $\Delta\alpha$. For $N_m$ evenly spaced measurements along the trajectory: $\Delta\alpha=\alpha(L_p)/N_m$ and $dL=L_p/N_m$. The relative rotation angle spread compared to $\Delta\alpha$ is $\delta\alpha(l)/\Delta\alpha=(2l/L_p)N_m/N_\lambda$ attaining a maximum value of $2N_m/N_\lambda$ at $L_p$. Another condition on $N_m$ and $N_\lambda$ is that $L_p=N_m N_\lambda \lambda_o$. The largest relative rotation angle spread compared to $\Delta\alpha$ is then $2\lambda_o N_m^2/L_p$ pessimistically rising quadratically with the number of measurements along the trajectory, $N_m$. To illustrate the magnitude of the rotation angle spread, three plasma scenarios that are relevant to the Magnetic Fusion Energy ("MFE") program are considered. The first two plasmas are in the High Energy Density Laboratory Plasma ("HEDLP") field and have exceptionally high densities, the third plasma is the future ITER tokamak device.

The FRX-L plasma, the target plasma of the Magnetized Target Fusion ("MTF") program.

Nominal parameters: $L_p=36$ cm, $n_{eo}=10^{23}$ m$^{-3}$, $B_o=5$ T, $dL=L_{pulse}=c\tau_{det}=1.8$ cm, $\lambda_o=3.2$ μm $N_m=20$, $N_\lambda=5,540$, $\alpha(L_p)=0.5$, $\Delta\alpha=\alpha(L_p)/N_m=0.025(1.5°)$ $N_m N_\lambda$=110,000! The largest relative rotation angle spread is 0.72%

The FRX-L compressed plasma

Nominal parameters: $L_p$=6 cm, $n_{eo}$=3×10$^{25}$ m$^{-3}$, $B_o$=500 T, dL=$L_{pulse}$=c$\tau_{det}$=3 mm, $\lambda_o$=46 nm
$N_m$=20, $N_\lambda$=65,000, $\alpha(L_p)$=0.5, $\Delta\alpha$=$\alpha(L_p)/N_m$=0.025 (1.5°)
$N_m N_\lambda$=1,305,000! The largest relative rotation angle spread is 0.060%

The International Thermonuclear Experimental Reactor ("ITER") tokamak device

Nominal parameters: $L_p$=4 m, $n_{eo}$=0.5×10$^{21}$ m$^{-3}$, $B_o$=0.5 T, dL=$L_{pulse}$=c$\tau_{det}$=20 cm, $\lambda_o$=31 μm.
$N_m$=20, $N_\lambda$=4,600, $\alpha(L_p)$=0.5, $\Delta\alpha$=$\alpha(L_p)/N_m$=0.025(1.5°)
$N_m N_\lambda$=92,000. The largest relative rotation angle spread is 0.86%

The relative rotation angle spreads in a due to dispersion are remarkably low for the three pulsed polarimeter measurement scenarios due to the large $n_{eo}B_o$ product. However, pulsed polarimetry would seem to have increasing difficulty with magnetized plasmas of low $n_{eo}B_o$ product. This is not necessarily the case as explained below.

A spread in rotation angle does not necessarily translate into a large measurement error in determining $\Delta\alpha$. For the collimated emission beam 37 with a rotation angle spread, $\delta\alpha$, the polarization detection system 30 determines the polarization state to be that given by the median electric field amplitude of the distribution of polarization components with intensity given by the total intensity of the distribution. For $\alpha(L_p)$<0.5(30°), symmetric distributions about the median rotation angle, $\alpha$(l) have little affect on the measurement of $\alpha$(l) and $\delta\alpha$ can be of the order $\alpha(L_p)$ or $\Delta\lambda$~$\lambda_o$ before sizeable errors are produced. For $\alpha(L_p)$>0.5, a rotation angle spread effects the measurement of $\alpha$(l) through the nonlinear sine and cosine functions and $\delta\alpha$ must be reduced by increasing $L_{pulse}$ which lowers the spatial resolution but increases the accuracy. The number of measurements $N_m$ for $\alpha(L_p)$=0.5 (30°) is dictated by the resolving power of the polarization detection system. If the noise sources allow, a polarimeter instrument should be able to determine α to a resolution of ~0.005° implying a dynamic range of 6000:1. There is a trade off between the number of measurements, $N_m$, and the accuracy of the magnetic field measurement. One could provide $N_m$=600 with 10% accuracy or $N_m$=100 with 1.6% accuracy. The pulsed polarimeter technique has the potential for exceptional spatial resolution and magnetic field accuracy for these three important magnetized plasmas.

ii) Noise Sources in General

All of the other sources of measurement error are under the experimenter's control and can be minimized up to the limits of technology and costs. For instance, the measurement SNR is directly proportional to the pulse energy, $E_{pulse}$. Pulse energy, $E_{pulse}$, and pulse power, $E_{pulse}/\tau_{pulse}$, can be very high before the pulsed polarimeter becomes perturbative but such light sources are costly. The main sources of noise are 1) the backscatter photon noise, 2) background plasma emission photon noise, 3) blackbody emission photon noise from surfaces in the field of view and 4) detector noise. The main methods used to minimize these sources of noise are:

1. Optically Filtering of Backscatter and Background Light

An optical band-pass frequency filter can be used to selectively accept the desired backscatter emission and reject the out-of-band background light, especially from light sources 2) and 3). A band-pass filter of width $\Delta v_{filter}/v_o$~2.5×10$^{-5}$√$T_e$ (4% for a 300 eV plasma) centered about $v_o$ is wide enough to accept most of the temperature broadened backscatter. A spread in rotation angle will result from the temperature wavelength broadening but will not affect the rotation angle measurement if the band-pass filter is symmetric about $v_o$.

Filtering the backscattered emission at a center frequency offset to $v_o$ will introduce a frequency dependent rotation angle offset due just to the rotation angle dispersion over the backscattered path. This can be exploited as a diagnostic when offset filtering is used as in a pulsed polarimeter system that spectrally resolves the backscatter emission to measure $T_e$.

2. Intrinsic Backscatter Photon Noise

The measurement SNR from intrinsic backscatter photon noise is √($\eta N_{sc}$) where $N_{sc}$ is the number of backscattered photons collected by the light gathering optic 49 of FIG. 2B. The photon noise (shot noise) is due to the discrete nature of light. The noise is minimized or measurement SNR maximized by selecting an optical detector with η close to 1, increasing $E_{pulse}$ or raising $\Delta\Omega$. Plasmas with high $n_e$ have the lowest backscatter photon noise making the HEDLP plasmas especially attractive.

3. Plasma Background Emission Photon Noise

Plasma emission for magnetized plasmas in the optical region is predominately broadband bremsstrahlung emission. Line radiation is narrow band and can be selectively filtered away. The contribution of bremsstrahlung emission with intensity, $I_b$, contributes $\eta I_b$/√($\eta N_{br}$) photon noise to the intrinsic backscatter photon noise and the measurement SNR is then given by √η $N_{sc}$/√($N_{sc}$+$N_{br}$), where $N_{br}$ is the number of bremsstrahlung photons collected by the light gathering optic 49 of FIG. 2B. The level of bremsstrahlung emission is proportional to the imaged volume ($\pi r_{image}^2 L_p$), $\Delta\Omega$, $n_e$,1/√$T_e$ and $\tau_{det}$. The bremsstrahlung photon noise is generally negligible for MFE plasmas due to the exceedingly low $\tau_{det}$(~100 ps) of a pulsed polarimeter.

4. Blackbody Emission Photon Noise

Blackbody emission from surfaces (windows, vacuum vessel, etc) at a temperature, $T_{surface}$, in the field of view of the light gathering optic 49 can be a significant source of noise if $\lambda_o$, is near the Wien wavelength, 2.9 mm/$T_{surface}$, as is the case for the $CO_2$ laser system at 10.6 μm ($\lambda_{Wien}$=10 μm for $T_{surface}$=300K, room temperature). The measurement SNR is then √η $N_{sc}$/√($N_{sc}$+$N_{br}$+$N_{bb}$), where $N_{bb}$ is the number of blackbody photons collected by the light gathering optic 49 of FIG. 2B together with any imaged surface in the pulsed polarimeter instrument. Blackbody emission can be significantly reduced by i) using polished metal surfaces to lower the surface emissivity, ii) cooling the surfaces in the field of view and iii) selecting a $\lambda_o$ far from the $\lambda_{Wien}$.

5. Detector Noise

Optical detectors have a minimum detectable signal level rating given by the optical detector's noise equivalent power ("NEP"). The NEP is bandwidth dependent. An NEP of 10$^{-11}$ W/Hz$^{1/2}$ or 1 μW for a 10 GHz $BW_{det}$ is typical. Cooling the optical detector reduces the NEP but also reduces the optical detector's bandwidth.

The measurement SNR is raised most easily by increasing $E_{pulse}$ or raising $\Delta\Omega$. The first is limited by technology or expense and the second by collecting scattered light that deviates more from the backward direction compromising the principles of the invention. The experimenter determines $\lambda_o$, $E_{pulse}$, $L_{pulse}$, $\tau_{det}$, $\Delta\Omega$, $\Delta v_{filter}$ and detector NEP to measure a magnetic field with a prescribed accuracy, $\delta B_\parallel/B_\parallel$, with spatial resolution given by dL.

The realized accuracy depends on both the measurement SNR and the minimum rotation angle that the polarization detection system 30 can resolve. Angular resolutions of 0.005° are possible. Given a measurement SNR of 1/∈ and an incremental rotation angle Δα, the relative accuracy of the magnetic field measurement $\delta B_\parallel/B_\parallel$ and density measurement $\delta n_e/n_e$ are given by:

$$\delta n_e/n_e = \epsilon \text{ and } \delta B_\parallel/B_\parallel = \epsilon/2\Delta\alpha \quad \text{Eq. 10}$$

From Eq. 10 one sees that the accuracy of the magnetic field can be improved by increasing the incremental rotation angle, Δα, with a corresponding increase in dL which decreases the spatial resolution of the measurement. The trading off of magnetic field accuracy for spatial resolution is intrinsic to the pulsed polarimetry technique.

EXAMPLE

FRX-L Plasma, the Target Plasma of the Magnetized Target Fusion (MTF) Program.

The FRX-L experiment at Los Alamos produces a field reversed configuration ("FRC") magnetized plasma with peak electron density, $n_{eo}$, of $10^{23}$ m$^{-3}$, and peak magnetic field, $B_o$, of 5 T. The FRC is highly transient, existing for only 10 μs's. The FRC is to be used as the target magnetized plasma in an imploding liner MTF experiment attaining a peak magnetic field of 500 T and peak $n_{eo}$ of $3\times10^{25}$ m$^{-3}$! There are no internal magnetic field diagnostics available for this program and CW plasma polarimetry is highly susceptible to mechanical and refraction phase noise. Conventional Thomson scattering measurements of $T_e$ have not been successful due to high bremsstrahlung levels but $T_e$ is thought to be ~300 eV (3 million° C.). Theoretical understanding of the FRC plasma is primitive in comparison to the tokamak plasma. External magnetic diagnostics and CW interferometry are the principal diagnostic systems. The pulsed polarimeter design below is realistic and realizable within the present technology.

FRX-L Pulsed Polarimeter Parameter List

| | |
|---|---|
| NdYag laser: | $\lambda_o$ = 1.064 μm, |
| Pulse energy | $E_{pulse}$ = 1J, |
| Pulse length | $L_{pulse}$ = 6 mm |
| Spectral width | Δλ < 1 nm |
| beam radius | $r_{beam}$ = 1 mm |
| $\Delta v_{filter}$ | 1.4 × $10^{13}$ Hz |
| dL | 3 cm |
| Δα | 0.009(0.52°) at peak $n_e$ = $10^{23}$ m$^{-3}$, B = 5 T |
| ΔΩ | 0.035 sr ($\theta_{\Delta\Omega}$ = 6°) |
| InGaAs detector: | $\tau_{det}$ = 100 ps, |
| | $BW_{det}$ = 2.25 GHz, |
| | max intensity = 5 mW, |
| | NEP = 1 μW@2.25 GHz |
| Backscatter | 4 W |
| Backscatter energy | 0.83 nJ |

| Noise level: | |
|---|---|
| Backscatter photon noise | 0.002%, |
| Bremsstrahlung photon noise | 4 × $10^{-16}$ J, negligible |
| Blackbody photon noise | negligible |
| Detector noise | 1 μW, negligible |
| Plasma details: | $v_o$ above cutoff frequency scattering is incoherent Thomson scattering |

In this case, the accuracy of the magnetic field measurement is limited by the optical detector's dynamic range: 5000:1. The backscatter intensity is too strong for the optical detector and must be attenuated from 4 W down to the 5 mW level.

With a 1 μW detector NEP:

| | |
|---|---|
| SNR | 5000 (∈ = 0.0002) |
| $n_e$ accuracy | $\delta I_o/I_o = \delta n_e/n_e$ = 0.02% |
| $B_\parallel$ accuracy | $\delta B_\parallel/B_\parallel = \epsilon/2\Delta\alpha$ or 1% |
| Spatial localization | 3 cm |

With a limiting optical detector dynamic range of 5000:1 a small rotation angle of 0.52° (1 part in 50) can be resolved to 1% (1 part in 100). The magnetic field accuracy $\delta B_\parallel/B_\parallel$ is then 1% with a spatial resolution of 3 cm or 12 measurement points over the 36 cm long plasma. A polarimeter resolution of 0.005° is assumed.

There is roughly 1000× more backscatter than the optical detector can handle. The pulsed polarimeter can take advantage of the excess backscatter by 1) adding a spectrometer and more optical detectors to measure the spectral distribution of the collimated emission beam 37 and thereby determine $T_e$, 2) reducing ΔΩ to better approximate pure backscatter, or 3) reducing dL to increase the spatial resolution if the resolution of the polarimeter detection system will allow.

The Non-Local Nature of Pulsed Polarimetry

Pulsed polarimetry uses a LIDAR technique to measure local $n_e(s)$. The $n_e$ measurement is truly local; the intervening remote magnetized plasma 54 between the polarized light pulse 42c and the polarization detection system 30 does not influence the measurement of $n_e$, no assumption that $n_e$ be quasi-static is necessary, uncertainty in the $n_e$ measurement does not accumulate with distance, and the $n_e$ measurement is direct. The rotation angle measurement, 2α(l,T), is, however, non-local, being the sum of two path integrals α(l,T) and $\alpha_r$(l,T) with identical locations contributing to the integrals at different times. For a quasi-static $n_e$ and quasi-static magnetic field, α(l,T)=$\alpha_r$(l,T) always and the local $n_e B_\parallel$(l) product can be obtained, not directly, but by differencing of two sequential non-local measurements of 2α(l,T). Obviously, for pulsed polarimetry, the intervening remote magnetized plasma 54 between the polarized light pulse 42c and the polarization detection system 30 determines the measurement.

There are implications for the pulsed polarimeter: 1) if the magnetic field or density is changing on a time scale shorter than 2l/c, then the two path integrals can be different and the measurement is not $n_e B_\parallel$(l) and 2) an uncertainty or spread in rotation angle grows with distance. In general the quasi-static criterion is fulfilled for magnetized plasmas of interest to the MFE field and the pulsed polarimetry measures local $n_e B_\parallel$. As for 2), $\lambda_o$ is chosen so that the maximum rotation angle, α($L_p$), is small for the particular application. It is a violation of quasi-static condition that allows pulsed polarimetry to be exploited for the remote sensing of electric fields in electro-optically active media. The optical activity in a medium with induced electro-optic activity is reciprocal and the pulsed polarimeter would produce a null measurement if the electric field were quasi-static.

Pulsed polarimetry provides a sequence of advancing chord averaged $n_e B_\parallel$(l) measurements that CW plasma polarimetry would provide if the retro-reflecting end mirror 22b of FIG. 1 could be translated through the remote magnetized plasma 28. Both methods are subject to the same quasi-static criterion. The magneto-optic Faraday effect has been shown to be an interference effect in both CW polarimetry and pulsed polarimetry. Every technique in CW polarimetry/interferometry has a counterpart in pulsed polarimetry if a coherent polarized light source is used. The pulsed polarimeter additionally measures local $n_e(l)$.

Review of Provisos for Pulsed Polarimetry

1) $B_\|(s) = B(s) \cdot \hat{s}$ is determined. As with CW plasma polarimetry, the orientation of the optic axis 44 of FIG. 2B with respect to the remote magnetic plasma 54 must be judiciously chosen, as is the case with CW plasma polarimetry.
2) Both B and $n_e$ must be quasi-static on a $2L_p/c$ time scale to determine local $B_\|(s.)$, as is the case with CW plasma polarimetry.
3) The light source wavelength, $\lambda_o$, should be set so that $\alpha(L_p) < \sim 0.5(30°)$. An $\alpha(L_p) > 0.5$ may cause the characteristic modes to spatially separate and a measurement error due to a spread in $\alpha(l)$ may result. The range of $\alpha(L_p)$ has to be assessed for the particular application.
4) Refractive effects will not affect the magnetic field or density measurements of a pulsed polarimeter but account must be taken of the location of the polarized light pulse 42c in the remote magnetized plasma 54 to interpret the measurements.
5) Other magneto-optic activity in magnetized plasmas, such as the Cotton Mouton effect, doesn't contribute to the $\alpha(l)$ measurement since this activity is reciprocal.
6) The collection angle, $\Delta\Omega$, should be kept as small as possible to better approximate backscatter. The range of $\Delta\Omega$ has to be assessed for the particular application.

SECOND EMBODIMENT

A second embodiment of the pulsed polarimeter is shown in FIG. 3. A remote magnetic field distribution in free space is to be measured remotely. To achieve this, the remote magnetized plasma 54, shown in FIG. 2B, is replaced with a remote magneto-optic medium 62 placed at the position where the magnetic field distribution 60 is to be determined. In the case of the remote magnetized plasma 54 of FIG. 2B, the magnetic field distribution 56 is produced by currents distributions both external and internal to the remote magnetized plasma 54. For the second embodiment of a pulsed polarimeter as shown in FIG. 3, the current distribution must lie totally outside of the remote magneto-optic medium 62. For a remote magneto-optic medium 62 that is non-conducting (an insulator), the free space magnetic field distribution 60 penetrates the remote magneto-optic medium 62 as if it were not there. The remote magneto-optic medium 62 can be a material with a determined Faraday effect specified by its material Verdet constant, V. Faraday rotator glass would be a good choice for a light source with a wavelength in the visible. V determines the rate of change of rotation angle, $\alpha(l)$, with distance for a given parallel magnetic field, B||, as given by:

$$a) \ \alpha(l, T) = V \int_0^l B_\|(s, t(s)) ds \qquad \text{Eq. 11}$$

and $$b) \ B_\|(l, T) = \frac{1}{V} \frac{d\alpha}{ds}\bigg|_l$$

The integration variable, s, corresponds to a time, $t(s) = Ns/c$, where N is the index of refraction of the remote magneto-optic medium 62. The total transit delay time is now $2NL_p/c$. Since the Faraday effect only depends on the magnetic field, a measurement of the intensity is unnecessary. The magnetic field profile is given by Eq. 11b). The magnetic field is assumed to be quasi-static on a $2NL_p/c$ time scale.

The effect is only weakly, if at all, dependent on $\lambda_o$ through V. Since the effect is only weakly dispersive, a large rotation angle spread does not result from a pulse length wavelength spread and the range of $L_{pulse}$ is unrestricted. The spatial resolution can be as high as the light source will allow. A useful application for the second embodiment is to provide a calibration target for a pulsed polarimeter. An inhomogeneous magnetic field distribution 60 can be intentionally produced in the remote magneto-optic medium 62 to diagnose the sensitivity and time resolution of a pulsed polarimeter intended for use on remote magnetized plasmas.

THIRD EMBODIMENT

A third embodiment of the pulsed polarimeter is shown in FIG. 3 where the remote magneto-optic medium 62 and the magnetic field distribution 60 is replaced by a remote electro-optic medium and an electric field distribution. An electric field, E, in a medium demonstrating induced electro-optic activity can produce an optical activity similar to the magneto-optic Faraday effect in a magneto-optic medium. A linear birefringence is induced by E producing a progressive rotation of the polarization of a polarized light pulse in the plane of polarization as the pulse propagates in the medium. Examples of electro-optic activity are the Kerr and Pockels effects. The electro-optic effect can depend on the electric field amplitude (linear effect), electric field intensity (quadratic effect), with the electric field either longitudinal or transverse to the trajectory. Many different electro-optic activities are possible, however, all are reciprocal, producing a net rotation angle of zero for backscatter as given by:

$$\alpha_E(l) = V_E \int_0^l E_\|(s, \frac{Ns}{c}) ds + V_E \int_l^0 E_\|\left(s, \frac{2Nl}{c} - \frac{Ns}{c}\right) ds = 0 \qquad \text{Eq. 12}$$

Eq. 12 illustrates a linear longitudinal electro-optic birefringence with strength given by the optical constant, $V_E$, where N is the index of refraction of the medium. The added paths integrals cancel for a reciprocal effect. This would seem to make a pulsed polarimeter useless for the remote and non-perturbative sensing of the local electric field in an electro-optic medium.

It may be the case, however, that the electric field is rapidly changing in time and is not quasi-static on a double path integral time $2Nl/c$. Then a pulsed polarimeter can provide a measurement of the temporal/spatial change of the electric field in the medium. Essentially, the rotation angle for the forward path, $\alpha_f(l)$, is not equal and opposite to the rotation angle of the return path, $\alpha_r(l)$, where $\alpha(l) = \alpha_f(l) + \alpha_r(l)$ because the electric field has changed in time and space along the trajectory during this time interval. This non-zero difference from summing the two path integrals is produced by both the temporal change in the electric field profile and also the ever-advancing path length. A time derivative of the measurement does not lead to any local details of the inducing electric field. The effect is only weakly if at all dispersive and so the pulse length, $L_{pulse}$, is not restricted in range and the spatial resolution can be as high as the light source will allow. An application for the third embodiment would be the measurement of the spatio-temporal evolution of the inducing electric field in an electro-optic medium, especially where the electric field distribution can be reproduced repeatedly with an advancing delay with respect to the timing of the polarized light pulse. The third embodiment exploits and illustrates the non-local nature of pulsed polarimetry by producing a non-local measurement of the temporal behavior of the inducing electric field in an electro-optic medium complementing the local measurement of the quasi-static inducing magnetic field in a magneto-optic medium.

Present Technology for Pulsed Polarimetry

Light Sources

Intense pulsed laser light sources exist from the Far Infrared ("FIR") (400 µm) through vacuum ultra-violet (100 nm) with power levels in the terawatt range (10 J in 10 ps, say) and even the petawatt level has been reached. The modest $CO_2$ pulsed laser (10.6 µm) can produce a 100 ps ($L_{pulse}$=3 cm) pulse at 1 J level, the NdYag laser (1.064 um), 10 ps ($L_{pulse}$=3 mm) pulse at 1 J, TiSapphire laser, 1 ps ($L_{pulse}$=0.3 mm) pulse at 800 nm and the optical lasers can be frequency doubled and quadrupled. The most suitable sources for the MFE field are light sources with a wavelength in the near infrared ("NIR") to FIR range (2 µm-50 µm) a role filled by the Free Electron Laser ("FEL"). An FEL would require a large infrastructure and is costly but can produce intense ultra-short pulses throughout the FIR and NIR making possible pulsed polarimetry for the future MFE program at the most advantageous wavelength. The extremely dense, high field plasmas in the HEDLP field will require developing the lowest wavelength ultra-short polarized pulsed lasers down to 30 nm. Incoherent light sources are also possible in this range for the very dense plasmas in the HEDLP field.

Detectors

Photodiode detectors in the NIR and visible have bandwidths as high as 60 GHz (0.1 mm) and 5 GHz (1.5 cm) for infrared ("IR") detectors. Real time data acquisition systems with 60 GHz bandwidths presently exist. The FIR range can use heterodyne techniques. Detector technology is advancing rapidly to keep pace with the bandwidth of the light sources used in the communications and fiber optics industries. These detectors can be used as mixers in the heterodyne mode which is an emerging technology.

Radiation Hazards and Serviceability

Diagnostics for ITER and other future burning plasma devices in the magnetic fusion energy field must be compatible with high neutron flux and use only components that are radiation compatible. The only plasma facing component in a pulsed polarimeter need be a metal or dielectric mirror for collecting light and aiming the pulse. The light pulse and collected light can be optically relayed to and from the plasma from a remote location where the detectors and sources are safe and serviceable. A LIDAR $n_e$ and $T_e$ diagnostic is planned for ITER.

Insight Needed for the Invention

How could such a key diagnostic technique be overlooked in such an active field? Insight was needed to realize that the two physical properties of optical scattering in the backward direction with the non-reciprocal nature of the Faraday effect could be effectively combined to make possible the remote sensing of the local magnetic field in a magneto-optic medium. Technology is another answer. The present invention is a new exploitation of the laser, specifically the lasers ability to produce an intense short polarized light pulse. Such lasers are available in the visible, NIR and IR regions of the optical spectrum where the Faraday effect is too weak to produce a measurable effect on most present-day magnetized plasmas. A third answer is the method. The method would seem to be a generalization of the LIDAR method that measures the local $n_e$ of the plasma remotely, but as mentioned, the pulsed polarimetry method uses a succession of non-local path dependent measurements of the $n_e B_\|$ product along the trajectory of the pulse and determining local $n_e B_\|$ by differentiating the non-local measurements in time, a much more convoluted method. The plasma parameter regime is the fourth answer. The magnetic field strength, electron density and machine size have continually increased over time and are finally reaching levels where pulsed polarimetry is feasible with the present laser technology.

Advantages

A number of advantages of the pulsed polarimeter embodiments described above over the prior art are expanded upon and summarized below.

(a) Providing a spatially resolved magnetic field measurement. The importance of determining the magnetic field distribution, $B_\|(s)$, over the chord averaged $<n_e B_\|>_{L_p}$ product of the prior art cannot be overstated. A direct magnetic field profile measurement without perturbing the magnetized plasma would be unique, novel and a major technological advance. As an illustration, FIG. 5 shows the intensity and rotation angle profiles measured by a pulsed polarimeter for the modeled magnetic field distribution shown in FIG. 6. The diamond point in FIG. 5 is the only data point from the prior art CW polarimeter instrument at a time associated with the profile measurement. One might surmise from that one datum that the magnetic field is positive and weak. On the contrary, the magnetic field amplitude is large and alternating in sign and highly modulated. From the magnetic field distribution, details of the current distribution can now be determined using Maxwell's equations, far beyond the ability of any existing measurement system. The present invention is particularly useful for the transient, dynamic magnetized plasmas of the HEDLP field where $n_e B_\|$ is very high, high instrument bandwidths are needed and conventional diagnostics have failed. There, pulsed polarimetry would provide unprecedented measurement capabilities.

(b) A spatially resolved electron density measurement. The electron density distribution, $n_e(s)$, is naturally and necessarily obtained by a pulsed polarimeter. The electron density distribution alone, is a highly sought after measurement. Spatial variations in density (density gradients) are of paramount importance in understanding energy confinement, transport, density limits and locating transport barriers deep within the plasma. The $n_e$ measurement is truly local and not subject to phase effects as in conventional CW plasma interferometry.

(c) A spatially resolved electron temperature measurement. With the addition of a spectrometer and more optical detector channels, a pulsed polarimeter can be naturally configured to provide a measurement of the local electron temperature profile, $T_e(s)$. The spatial distributions of $B_\|$, $T_e$ and $n_e$ can be simultaneously measured in one instrument. The measurement of $T_e$, as with $n_e$, is a local measurement. For plasmas in the HEDLP field, conventional Thomson scattering diagnostics fail due to the high background plasma emission leaving this research field without a basic $T_e$ measurement method. Pulsed polarimetry is better able to measure $T_e$ due to the high pulse energies, large backscatter levels and the high detector bandwidths that effectively exclude, by a thousand fold, the background plasma emission that would overwhelmingly pollute a conventional Thomson scattering system.

(d) Very high temporal bandwidths. The pulsed polarimeter profile measurement is extremely quick, nearly instantaneous, requiring twice the medium transit time, $2L_p/c$, for the polarized light pulse. It would be difficult to justify imposing such a high bandwidth on a measurement system if it were not intrinsic to the technique. The magnetic field and density distributions are reasonably assumed quasi-static. The dynamical evolution of the magnetic structure can be followed by making multiple pulsed polarimeter profile measurements.

(e) A method for feedback control. A pulsed polarimeter can make a significant impact on the feedback control of magnetized plasmas in the MFE field. Pulsed polarimetry provides a means for a rapid real-time, almost instantaneous, direct magnetic field measurement that not only detects the presence of a destructive MHD instability but, just as importantly, localizes the disturbance so that corrective measures can be effectively applied.

(f) The elimination of coherent effects in the prior art. The interferometer of the prior art CW polarimeter/interferometer system shown in FIG. 1 requires a coherent light source. Interferometers are notoriously sensitive to displacements in optical components and beam misalignments during a measurement. A pulsed polarimeter uses polarized light pulse induced backscatter from the medium and is not affected by interference or phase effects.

Beam misalignments during a measurement are also successfully addressed by a pulsed polarimeter. Refraction due to density gradients in the magnetized plasma can displace (curve) the trajectory of the probe beam in the magnetized plasma introducing an unknown change in path length with a consequent phase shift and displace the probe beam on the retro-reflecting end mirror 22b of FIG. 1 which can affect the intensity amplitude at the optical detectors 12a,b. Both the interferometer and polarimeter measurements of a prior art CW polarimeter/interferometer can be seriously compromised. The pulsed polarimeter measures electron density and rotation angle along the displaced trajectory unaffected by phase effects and the backscatter retraces the refracted trajectory eliminating misalignments to first order.

(g) An improved interpretation of measurements. Both the prior art CW polarimeter/interferometer and pulsed polarimeter instruments exploit the magneto-optic Faraday effect. The standard formula interpreting the rotation angle as a chord averaged electron density-magnetic field product assumes the frequency of the light source is much higher than any cutoff frequency along the trajectory. If this is not the case, a useful interpretation of the measurement depends on the density profile along the trajectory. For a pulsed polarimeter, the local density profile is determined without approximation. The pulsed polarimeter can interpret the rotation angle measurements using a more exacting formula that incorporates the density profile and subsequently take advantage of light sources with wavelengths much closer to a cutoff.

(h) The remote sensing of vacuum magnetic fields. The pulsed polarimeter can be used to remotely measure the magnetic field distribution in free space by placing a surrogate magneto-optically active medium at the position where the magnetic field is to be determined. As long as the medium is insulating and lies outside of the magnetic field generating currents, the magnetic field distribution is identical to that of the free space distribution.

(i) Unbounded sightline. The prior art CW polarimeter shown in FIG. 1 requires encompassing the magnetized plasma between the directional coupler (non-polarizing beam splitter) 26 and the end mirror 22b. A single pass CW polarimeter would substitute an optical detector for the end mirror 22b. The pulsed polarimeter embodiments of the present invention do not require equipment along the optic axis beyond the medium. As shown in FIG. 2B, with the unbounded optic axis 44, one need only aim the optic axis into the remote magnetized plasma 54 to make a magnetic field profile determination along the resulting trajectory. This implies that every probe beam trajectory of interest in CW polarimetry is also available as a polarized light pulse trajectory for a pulsed polarimeter, conversely many more trajectories are available to a pulsed polarimeter. Access problems are considerably simplified. In FIG. 2B, a steering mirror can be introduced between the light gathering optic 49 and the remote magnetized plasma 54 to point the polarized light pulse 42b to and collect backscatter from any direction in which the optic axis 44 intersects the remote magnetized plasma. As a further exploitation of this idea, a steering mirror can be introduced beyond the plasma to redirect the polarized light pulse through the plasma a second time to measure a magnetic field profile along a second sightline.

It may be the case that the probe beam will not exit the magnetized plasma due to a plasma cutoff at some location along the trajectory. In that case the CW polarimeter/interferometer is useless but a pulsed polarimeter can, in theory, provide local density and magnetic field measurements up to the location of the cutoff along the trajectory (j) Next step devices. Future laboratory magnetized plasmas will be more challenging to diagnose. The direction in tokamak development in the MFE program is larger size, higher magnetic field and higher density and achieving ignition (burning plasmas). ITER is the next scale in tokamak devices. The pulsed polarimetry technique thrives on the new devices since the Faraday effect is stronger (larger $n_e B_\parallel$ product) but also the pulse length can be longer and maintain the same relative size to the device thereby simplifying the light source.

(k) The HEDLP research field. In the HEDLP field, the magnetized plasmas are compressed to very small dimensions (~10 cm) and with enormous magnetic fields and densities. The density is so high that light sources in the visible and NIR must be used to be above cutoff. Even at optical wavelengths, the Faraday effect is strong enough to produce a measurable effect. Fortunately powerful pulsed lasers in the visible are well developed and pulse lengths on the order mm's-cm's are readily available and well suited for these magnetized plasmas. Pulsed polarimetry has a unique opportunity to play a major role in the understanding of MHD stability and dynamics of HEDLP magnetized plasmas. For one thing, the choice of diagnostics for these devices is exceedingly poor as many conventional diagnostics cannot be used, even the conventional Thomson scattering is overwhelmed by background plasma emission from the exceedingly high densities. The diagnostics that can be applied are usually much more demanding given the short time scales. However, the exceptionally high $n_e$ and $n_e B_\parallel$ product of HEDLP plasmas enhance the performance of the pulsed polarimeter enormously. Also, the time resolution of a pulsed polarimeter is exceptionally high, 660 ps transit time for $L_p$=10 cm. The magnetic field profile measurements are fast enough to resolve the dynamics of even these extremely transient plasmas. The backscatter levels are so high that the emission must be attenuated. The plasma cross section so small that one could imagine using a large diameter polarized light pulse with $r_{beam}$ larger than the plasma radius to illuminate the entire plasma cross section and a 2-d(r,θ) array of pulsed polarimeter systems to provide a 3-d image of $B_\parallel(r,\theta,z,T)$, $n_e(r,\theta,z,T)$ and $T_e(r,\theta,z,T)$ which would make these magnetized plasmas the best diagnosed. Pulsed polarimetry is well suited to this research and could improve the understanding of these plasmas in significant ways.

(l) Radiation capability. Deuterium-tritium fuel will be burned in the ITER plasma producing gigawatts of fusion power for 10's of minutes, exposing diagnostics to high neutron fluxes and activating the vessel. Remote handling methods will be a key development to keep ITER running. Diagnostics will have to be easily serviced by remote handling. One cannot envision a more compatible diagnostic than the pulsed polarimeter other than the LIDAR Thomson scattering diagnostic for interfacing with such a harsh environment. The light pulses can be sourced as remote from the magnetized plasma as necessary, the light pulse being relayed by mirrors and aimed to the required location by a final steering mirror in the torus and the emission being similarly collected. The polarized light pulse trajectory can be steered by the final steering mirror to provide wide access to the magnetized plasma.

In the case of HEDLP research, the radiation hazards are also severe when the plasma is fully compressed. In this case the plasma burn takes place in microseconds and is intense. The magnetized plasma confinement vessel is destroyed in the compression process. Two strong arguments for remotely sited optical instruments.

The present invention shows great promise to make significant contributions to the magnetic confinement field on all future high performance devices.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A pulsed polarimeter for conducting remote, non-perturbative diagnostic measurements of inducing fields of a medium demonstrating induced optical activity, the pulse polarimeter comprising:
   a light source configured to emit a polarized light pulse having sufficiently narrow spatial extent and at a prescribed wavelength;
   a light gathering optical system including:
      a light gathering optic having a optic axis directed toward the medium and positioned so that a predetermined solid angle of an emission from the medium is collected and collimated into a collimated emission beam, wherein the light gathering optic preserves the polarization state of the emission;
      a directional coupler configured to make coincident the propagation direction of the polarized light pulse with the optic axis of the light gathering optic and direct the polarized light pulse toward the medium; and
   a polarization detection system configured to measure the intensity and determine the polarization state of the collimated emission beam continuously in time as the polarized light pulse transits the medium, wherein the intensity and polarization state can be used to determine the inducing fields.

2. The pulsed polarimeter claim 1 wherein the light gathering optical system further comprises a collimating optic configured to collimate the emission from the light gathering optic into the collimated emission beam.

3. The pulsed polarimeter of claim 1 wherein the light source further comprises one or more of:
   a laser;
   a coherent laser; and
   an incoherent light source.

4. The pulsed polarimeter of claim 1 wherein the polarized light pulse emitted from the light source further comprises one or more of:
   linearly polarized light;
   circularly polarized light; and
   elliptically polarized light.

5. The pulsed polarimeter of claim 1 wherein the polarized light pulse emitted from the light source is frequency modulated.

6. The pulsed polarimeter of claim 1 wherein the directional coupler further comprises one of:
   a curved or planar reflective surface;
   a plane mirror with a hole;
   a non-polarizing beamsplitter; and
   a frequency selective reflecting surface.

7. The pulsed polarimeter of claim 1 wherein the light gathering optical system further comprises:
   a reflecting light gathering optic having a hole on axis with the optic axis and is configured to focus the emission; and
   a reflecting collimating optic positioned to receive and collimate the emission into the collimated emission beam that is transmitted through the hole of the light gathering optic.

8. The pulsed polarimeter of claim 1 wherein the light gathering optical system further comprises:
   a light gathering optic lens configured to focus the emission; and
   a light collimating optic lens positioned to receive and collimate the focused light pulse induced emission into the collimated emission beam.

9. The pulsed polarimeter of claim 1 wherein the polarization preserving optical system further comprises:
   a reflecting light gathering optic configured to focus the emission; and
   a light collimating optic lens positioned to receive and collimate the focused light pulse induced emission into the collimated emission beam.

10. The pulsed polarimeter of claim 1 wherein the polarization detection system further comprises:
    a polarizing beam splitter configured to analyze and separate the collimated emission beam into a first collimated polarized beam and a second collimated polarized beam polarized orthogonally to the first collimated polarized beam;
    a first focusing lens configured to receive and focus the first collimated polarized beam;

a second focusing lens configured to receive and focus the second collimated polarized beam;

a first detector positioned to detect the focused first collimated polarized beam and produce an electrical signal that is proportional to the intensity of the first collimated polarized beam; and a second detector positioned to detect the focused second collimated polarized beam and produce electrical signal that is proportional to the intensity of the second collimated polarized beam.

11. The pulsed polarimeter of claim 1 wherein the optically active medium demonstrating induced optical activity further comprises one of:

a magnetized laboratory plasma and the magneto-optical Faraday effect;

an optically transparent medium demonstrating the magneto-optical Faraday effect;

an optically transparent medium demonstrating the electro-optical Kerr effect; and an optically transparent medium demonstrating the electro-optic Pockels effect.

12. The pulsed polarimeter of claim 1 wherein the intensity and polarization state can be used to determine the inducing fields further comprises one of:

determine a spatial distribution of an magnetic field along the trajectory of the polarized light pulse when the medium is in a magneto-optically active medium with location given by time-of-flight; and determine a spatio-temporal development of an electric field along the trajectory of the polarized light pulse when the medium is an electro-optically active medium with location given by time-of-flight.

13. A method of conducting remote, non-perturbative diagnostic measurements of the inducing fields of a medium demonstrating induced optical activity, the method comprising:

generating a polarized light pulse having sufficiently narrow spatial extent and at a prescribed wavelength;

collecting a predetermined solid angle of an emission from the medium along a optic axis of a light gathering optic and collimating the emission into a collimated emission beam while preserving the polarization state of the emission;

making coincident the propagation path of the polarized light pulse with the optic axis of the light gathering optic and directing the polarized light pulse toward the medium; and determining the inducing fields based on measuring the intensity and determining the polarization state of the collimated emission beam continuously in time as the polarized light pulse transits the medium.

14. The method of claim 13 wherein the polarized light pulse further comprises one or more of:
linearly polarized light;
circularly polarized light; and
elliptically polarized light.

15. The method of claim 13 wherein generating the polarized light pulse further comprises frequency modulating the polarized light pulse.

16. The method of claim 13 wherein directing the polarized light pulse toward the optically active medium along the axis of the solid angle further comprises reflecting the polarized light pulse off of a reflective surface.

17. The method of claim 13 wherein collimating the polarized light pulse induced emission further comprises:
gathering the light pulse induced emission; and
reflecting the gathered light pulse induced emission into the collimated emission beam.

18. The method of claim 13 wherein determining the intensity and the polarization state of the collimated emission beam further comprises spatially separating and resolving the collimated emission beam into a first collimated polarized beam and a second collimated polarized beam, wherein the polarization state of the first collimated polarize beam is orthogonal to the polarization state of the second collimated polarized beam.

19. The method of claim 13 wherein the optically active medium further comprises one of:

a magnetized laboratory plasma and the magneto-optical Faraday effect;

an optically transparent medium demonstrating the magneto-optic Faraday effect an optically transparent medium demonstrating the electro-optical Kerr effect; and an optically transparent medium demonstrating the electro-optic Pockels effect.

20. The method of claim 13 wherein determining the inducing fields further comprises one of:

determining a spatial distribution of an magnetic field along the propagation path of the polarized light pulse when the medium is a magneto-optically active medium with location given by time-of-flight; and determining a spatio-temporal development of an electric field along the propagation path of the polarized light pulse when the medium is an electro-optically active medium with location given by time-of-flight.

* * * * *